(12) United States Patent
Collin

(10) Patent No.: US 6,767,890 B1
(45) Date of Patent: Jul. 27, 2004

(54) PEPTIDES HAVING ANTI-CANCER AND ANTI-INFLAMMATORY ACTIVITY

(75) Inventor: Peter Donald Collin, Sunset, ME (US)

(73) Assignee: Coastside Bio Resources, Stonington, ME (US)

( * ) Notice: Subject to any disclaimer, the term of this patent is extended or adjusted under 35 U.S.C. 154(b) by 0 days.

(21) Appl. No.: 09/856,243

(22) PCT Filed: Nov. 18, 1999

(86) PCT No.: PCT/US99/27289

§ 371 (c)(1),
(2), (4) Date: Jul. 25, 2001

(87) PCT Pub. No.: WO00/29009

PCT Pub. Date: May 25, 2000

Related U.S. Application Data

(60) Provisional application No. 60/109,139, filed on Nov. 18, 1998, and provisional application No. 60/157,078, filed on Oct. 1, 1999.

(51) Int. Cl.[7] .................... A61K 38/00; A61K 38/08; C07K 7/06
(52) U.S. Cl. .......................... 514/2; 530/330
(58) Field of Search .................. 424/520; 514/2, 514/9, 11, 15–18, 8; 530/301, 317, 321, 326–330

(56) References Cited

U.S. PATENT DOCUMENTS

| | | | |
|---|---|---|---|
| 4,816,449 A | * | 3/1989 | Hahn .......................... 514/17 |
| 5,770,205 A | * | 6/1998 | Collin ........................ 424/520 |
| 5,912,233 A | * | 6/1999 | Hahn .......................... 514/17 |
| 5,945,033 A | * | 8/1999 | Yen ............................ 424/1.29 |
| 5,965,526 A | * | 10/1999 | Wakimasu et al. ............ 514/11 |
| 6,172,096 B1 | * | 1/2001 | Gregory et al. |

FOREIGN PATENT DOCUMENTS

WO    WO 98/17301    *    4/1998

OTHER PUBLICATIONS

Bowie et al., "Deciphering the Message in Protein Sequences: Tolerance to Amino Acid Substitutions," Science, vol. 247, pp. 1306–1310 (1990).*
CancerWEB On–line Medical Dictionary, "Inflammatory Response", and "Lymphocyte" 2002.*
Bowie et al., Science, vol. 247, pp. 1306–1310 (1990).*

* cited by examiner

Primary Examiner—James Housel
Assistant Examiner—Zachariah Lucas
(74) Attorney, Agent, or Firm—Rothwell, Figg, Ernst & Manbeck

(57) ABSTRACT

A pentapeptide is disclosed having the generic formula A-A-A-B-C (SEQ ID NO:2) wherein A is a non-polar amino acid, B is a polar amino acid, and C is a charged amino acid. In a preferred embodiment the peptide has the sequence A-Pro-Pro-B-C (SEQ ID NO:3), and in a further preferred embodiment has the sequence of leucine-proline-proline-serine-argenine (SEQ ID NO:1). In a most preferred embodiment, the peptide comprises at least one D-amino acid. The peptide can be extracted from the epidermis of sea cucumbers. The peptides of the present invention are useful for inhibition of tumor progression and/or inflammation in a mammal by administration from 1 milligram per kilogram body weight to 5000 milligrams per kilogram body weight. The peptide can be administered in conjunction with any suitable carriers or excipients as are known those skilled in the arts via oral delivery forms, such as in capsules, drinks, powders, rectally via suppositories, or other suitable means.

10 Claims, 4 Drawing Sheets

SEQUENCE LISTING

<160> NUMBER OF SEQ ID NOS: 3

<210> SEQ ID NO 1
<211> LENGTH: 5
<212> TYPE: PRT
<213> ORGANISM: Homo sapiens

<400> SEQUENCE: 1

Leu Pro Pro Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Generic Formula
<221> NAME/KEY: MISC_FEATURE
<222> LOCATION: (1)..(1)
<223> OTHER INFORMATION: Xaa = a non-polar amino acid
<221> NAME/KEY: MISC_FEATURE
<222> LOCATION: (2)..(2)
<223> OTHER INFORMATION: Xaa = a non-polar amino acid
<221> NAME/KEY: MISC_FEATURE
<222> LOCATION: (3)..(3)
<223> OTHER INFORMATION: Xaa = a non-polar amino acid
<221> NAME/KEY: MISC_FEATURE
<222> LOCATION: (4)..(4)
<223> OTHER INFORMATION: Xaa = a polar amino acid
<221> NAME/KEY: MISC_FEATURE
<222> LOCATION: (5)..(5)
<223> OTHER INFORMATION: Xaa = a charged amino acid

<400> SEQUENCE: 2

Xaa Xaa Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Generic Formula
<221> NAME/KEY: MISC_FEATURE
<222> LOCATION: (1)..(1)
<223> OTHER INFORMATION: Xaa = a non-polar amino acid
<221> NAME/KEY: MISC_FEATURE
<222> LOCATION: (4)..(4)
<223> OTHER INFORMATION: Xaa = a polar amino acid
<221> NAME/KEY: MISC_FEATURE
<222> LOCATION: (5)..(5)
<223> OTHER INFORMATION: Xaa = a charged amino acid

<400> SEQUENCE: 3

Xaa Pro Pro Xaa Xaa
1               5

PEPTIDES HAVING ANTI-CANCER AND ANTI-INFLAMMATORY ACTIVITY

This application is a 371 application of PCT/US99/27289, filed on Nov. 18, 1999, and claims priority to Provisional Application 60/109,139, filed Nov. 18, 1998, and to Provisional Application 60/157,078, filed on Oct. 1, 1999.

TECHNICAL FIELD

The present invention relates to the fields of cancer treatment, inflammatory disease, and peptide chemistry.

BACKGROUND

The amino acid sequence Leu-pro-pro-ser-arg (SEQ ID NO:1) is a known immunostimulant and is described in papers by W. Weigle and is the subject of a US Patent. Briefly, the sequence of the present invention has been examined in U.S. Pat. No. 4,683,221 and claims were made for the stimulation of lymphocyte proliferation in mammals. U.S. Pat. No. 4,683,221 is included herein by reference, and contains descriptions of the biological effects of the SEQ. ID. 1 with regards to B cells, B cell differentiation and macrophages in vivo and in vitro experiments. Nowhere in the Weigle patent is mention of angiogenesis inhibition nor the connection between lymphocyte activiation and the inhibition of human neoplasms nor inflammation inhibition. Based on the work described in the Weigle patent, one would anticipate that the strong immuno-stimulating effect of the peptide leu-pro-pro-ser-arg (SEQ ID NO:1) would lead to increased inflammatory response.

Also, the Weigle patent does not describe any production methods of the subject peptide as being available from sea cucumber epithelial or other tissue.

Angiogenesis is the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system. Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease mediated by angiogenesis is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues.

Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone arrow in which unrestrained proliferation of white blond cells occurs, usually accompanied by anemia, irpaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows minor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several kinds of compounds have been used to prevent angiogenesis. Taylor et al. have used protamine to inhibit angiogenesis, see Taylor et al., Nature 297:307 (1982). The toxicity of protamine limits its practical use as a therapeutic. Folkman et al. have disclosed the use of heparin and steroids to control angiogenesis. See Folkman et al., Science 221:719 (1983) and U.S. Pat. Nos. 5,001,116 and 4,994,443. Steroids, such as tetrahydrocortisol, which lack gluco and mineral corticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors such as interferon inhibit angiogenesis. For example, interferon .alpha. or human interferon .beta. has been shown to inhibit tumor-induced angiogenesis in mouse dermis stimulated by human neoplastic cells. Interferon .beta. is also a potent inhibitor of angiogenesis induced by allogeneic spleen cells. See Sidky et al., Cancer Research 47:5155–5161 (1987). Human recombinant .alpha. interferon (alpha/A) was reported to be successfully used in the treatment of pulmonary hemangiomatosis, an angiogenesis-induced disease. See White et al., New England J. Med. 320:1197–1200 (1989).

Other agents which have been used to inhibit angiogenesis include ascorbic acid ethers and related compounds. See Japanese Kokai Tokkyo Koho No. 58-131978. Sulfated polysaccharide DS 4152 also shows angiogenic inhibition. See Japanese Kokai Tokkyo Koho No. 63-119500. A fungal product, fumagillin, is a potent angiostatic agent in vitro. The compound is toxic in vivo, but a synthetic derivative, AGM 12470, has been used in vivo to treat collagen II arthritis. Fumagillin and O-substituted fumagillin derivatives are disclosed in EPO Publication Nos. 0325199A2 and 0357061A1.

The above compounds are either topical or injectable therapeutics. Therefore, there are drawbacks to their use as a general angiogenic inhibitor and lack adequate potency. For example, in prevention of excessive wound healing, surgery on internal body organs involves incisions in various structures contained within the body cavities. These wounds are not accessible to local applications of angiogenic inhibitors. Local delivery systems also involve frequent dressings which are impracticable for internal wounds, and increase the risk of infection or damage to delicate granulation tissue for surface wounds.

Thus, a method and composition are needed that are capable of inhibiting angiogenesis and which are easily administered. A simple and efficacious method of treatment would be through the oral route. If an angiogenic inhibitor could be given by an oral route, the many kinds of diseases discussed above, and other angiogenic dependent pathologies, could be treated easily. The optimal dosage could be distributed in a form that the patient could self-administer.

Inflammation is a major contributor to many diseases and as such, methods and compositions of matter have been sought to mitigate the detrimental effects of inappropriate activation.

Dermal inflammation is partially mediated via the conversion of phospholipids to either endoperoxides and consequently prostaglandins via cyclooxygenase and 5-HETE's, or consequently leukotrienes via lipoxygenase (Kraghball and Voorhees. 1985. Curr. Probl. Derm. 13:1–10). Inhibition of either or both of these pathways is the means by which non-steroidal anti-inflammatory agents prevent an inflammatory response. Anti-inflammatory steroids act by inhibiting the release of arachidonic acid which can then be converted via either pathway to mediators of inflammation (Blackwell et al. 1980 Nature 287:147–149). It has been proposed that cytokines also mediate the inflammatory process and a better, or at least, equivalent inhibition of the inflammatory response may be achieved by inhibiting either cytokine production or the inhibition of the interaction of cytokines with their receptors on the cell surface of the inflammatory cell infiltrate. There have been several peptides isolated from sea cucumber of various species (Bizenheide, R., Tamori, Motokawa, et al. "Peptides Controlling Stiffness of Connective Tissue in Sea Cucumbers." Bio. Bull 194:253–259. June 1998), but none are reported to have the sequence of the peptides of the present invention, nor do any peptides that has as its activity, the ability to inhibit an inflammatory response in a mammal. As a potentiator of a mammalian immune system response by way of activating lymphocytes and B cells and the associated cascades of immune-system protection, the peptide of the present invention may exert its anti-inflammatory and anti-cancer effects by an up-regulation of the mammalian immune system that is then able to destroy cancer cells directly or competitively bind to Fc receptors, thus mitigating their biological effects.

SUMMARY OF THE INVENTION

The present invention relates to a peptide, defined by the generic formula A-A-A-B-C (SEQ ID NO:2), wherein A is a non-polar amino acid, B is a polar amino acid and C is a charged amino acid. A sub-group of these peptides can be described by the formula A-Pro-Pro-B-C (SEQ ID NO:3), wherein A, B,& C have the meanings defined above. A specific embodiment of the peptide comprises the sequence LEU-PRO-PRO-SER-ARG (SEQ ID NO: 1), which and is a fragment of various immunogammaglobulins, and especially of IgG, and described in U.S. Pat. No. 4,683,221 by William Weigle, et al as a portion of the Fc region of IgG. This peptide was initially isolated from the epidermis of the sea cucumber *Cucumaria frondosa*, and has both anti-cancer and potent anti-inflammatory activities. In a preferred embodiment the peptide comprises at least one D-amino acid.

DETAILED DESCRIPTION

Figure 1:
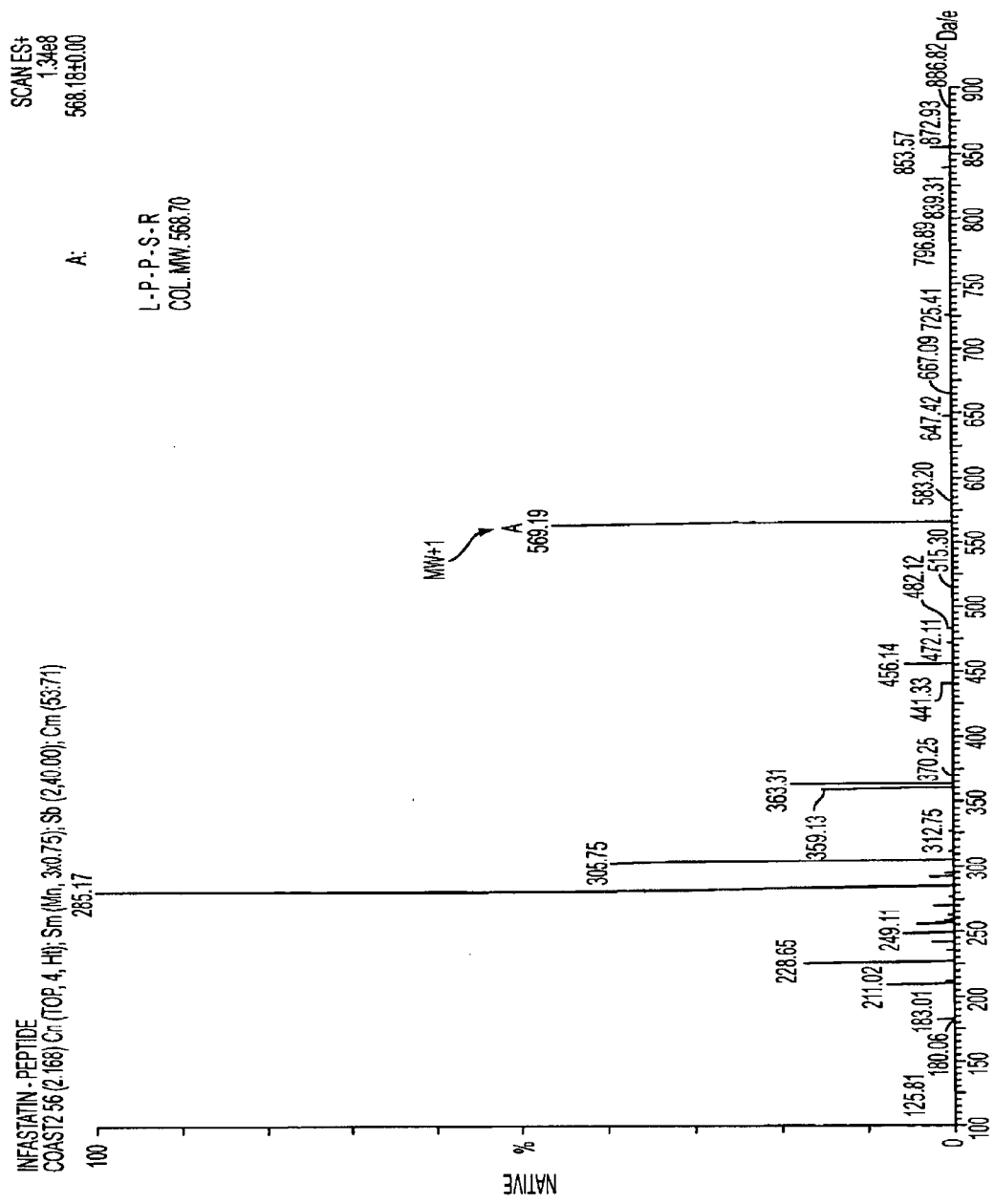
FIG. 1 shows the mass spectroscopy spectrum of the purified peptide.

The present invention relates in part to the anti-cancer activity of peptides and peptide derivatives related to defense mechanisms present on the epithelia of echinoderms and especially, of the sea cucumber, *Cucumaria frondosa*. The invention includes both pharmaceutical compositions comprising said peptides, and methods for inhibiting tumor progression utilizing said peptides. The invention is based in part on the discovery that the pentapeptide LEU-PRO-PRO-SER-ARG (SEQ. ID NO: 1) and analogues have potent anti-cancer activity as evidenced by activity in various screening assays such as those evaluating tumor necrosis factor (TNF-α) and interleukin-2 (IL-2) response, the inhibition of cancer as evidenced in a murine model of Sarcoma 180, the inhibition of angiogenesis as evidenced in the CAM assay of neovascularization. These two activities are correlated to anti-cancer effect. (See, e.g., "T-Cell Activation as Cancer Treatment," Conrad Notes (http://www./meds.com/conrad/ecco/nielsen.html) (1999) (presented at the European Cancer Conference (ECCO 9), Sep. 14–18, 1997).

Contrary to what would be expected from the teachings of the Weigle patent, the peptides of the present invention also may be used to inhibit inflammation in a tissue of a subject in need of such treatment suffering from a disease or disorder in which either acute or chronic inflammatory cell influx occurs. While not wishing to be bound by theory, this unexpected effect is believed to be due to the presence of one or more D-conformation amino acids in the sequence of the peptide isolated from sea cucumber, which alters the competitive binding of this peptide with receptor sites. The subject may be a human or non-human subject. Specific conditions in which peptides of the invention may have therapeutic value would include situations in which undesirable immune response has occurred, including, but not limited to, autoimmune diseases such as insulin-dependent diabetes, Goodpasture's syndrome, pemphigus and pemphigoid, primary biliary cirrhosis, ulcerative colitis, rheumatoid arthritis, scleroderma, mixed connective tissue disease and lupus erythematosus; graft versus host disease; septic shock; reperfusion injury (including injury subsequent to myocardial or cerebral infarction atherosclerosis; asthma, psoriasis and inflammatory lung disease. In preferred specific embodiments of the invention the peptide used to inhibit inflammation is SEQ. NO. 1 (Leu, Pro, Pro, Ser, Arg). This embodiment of the invention is based in part on the discovery that the peptides have potent anti-inflammatory activity, as evidence by a number of in vivo and in vitro tests, as well as from the realization that the tissue of origin of this peptide contains potent anti-inflammatory activity (U.S. Pat. No. 5,770,205).

The peptides of the invention include any peptide, peptide derivative or peptide analog which comprises either (i) as least three amino acid residues of SEQ. ID NO: 1, or (ii) a functionally equivalent sequence, or (iii) at least a 4 amino acid sequence which is at least 66% homologous to the corresponding portion of SEQ. ID NO. 1. Analysis of preparations of the peptide purified from sea cucumber indicate the presence of at least one D-amino acid in the sequence.

Peptides of the present invention can be described generically by the formula A-A-A-B-C (SEQ ID NO:2), wherein A is a non-polar amino acid, B is a polar amino acid and C is a charged amino acid. A sub-group of these peptides can be described by the formula A-Pro-Pro-B-C (SEQ ID NO:3), wherein A, B, & C have the meanings defined above. In the preferred embodiments of the invention, the peptide of the present invention, or its derivatives or analogs, comprises the sequence leucine-proline-proline-serine-arginine. The invention also refers to peptides in which certain residues are substituted by functionally equivalent amino acids resulting in a silent change. For example, one or more amino acids residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. In a preferred embodiment, the peptide comprises at least one D-amino acid.

The peptides of the present invention may be prepared by any method known in the art. For example, and not by way of limitation, the peptides may be synthesized: (i) by cleavage from a large peptide; (ii) by recombinant DNA expression methods; and (iii) by chemical synthesis, including solid phase techniques as described by Barany and Merrifield (1980 in "The Peptides: Vol. 2." Gross and Meienhofer, Eds., Academic Press, N.Y.).

The peptides of the invention may be administered by any suitable and accepted route of drug administration, including intravenous, subcutaneous, intradermal, intranasal, inhalation, intramuscular, intraocular, intraperitoneal injection, peritoneal lavage intranasal, inhalation, intramuscular, intraocular, intraperitoneal injection, peritoneal lavage, cardiac puncture, cardiac catheter injection, oral, intrathecal or intraventricular injection, spinal column or cranial cavity injection, vaginal or rectal dermal patch or topical ointment, and may be comprised in any suitable pharmaceutical carrier, including aqueous solution, micrbcapsules, liposomes, or via a sustained-release implant, including hydrophilic or hydrophobic carrier-based implants.

The compositions of the invention may be presented in pharmaceutical dosage forms normally used, depending on whether the composition has to be swallowed, injected or applied to the skin or mucosae.

For injection, the composition may take the form of an aqueous or oily lotion or the form of a serum.

For swallowing, the composition may take the form of capsules, syrup granules or tablets, or it can be incorporated appropriately into food-stuffs as a supplement to the food composition.

In the topical compositions of the invention, the peptide can preferably be used in an amount ranging from 1% to 100% by weight relative to the total weight of the composition, and especially in an amount ranging from 1% to 20% by weight relative to the total weight of the composition.

For topical application, the composition may take the form, in particular, of aqueous or oily solutions or of dispersions of the lotion or serum type, of emulsions, of liquid or semi-liquid consistency of the milk type, obtained by dispersing a fatty phase in an aqueous phase (O/W) or vice versa (W/O), or of suspensions or emulsions of soft consistency of the cream or aqueous gel type or which are anhydrous, of microemulsions or alternatively of microcapsules or microparticles, or of vesicular dispersions of the ionic and or nonionic type. These compositions are prepared according to the standard methods.

It may also be used for the scalp in the form of aqueous, alcoholic or aqueous-alcoholic solutions, or in the form of creams, gels, emulsions or foams, or alternatively in the form of aerosol compositions also containing a propellant agent under pressure.

In a known manner, the pharmaceutical or dermatological composition of the invention can also contain adjuvants which are customary in the fields in question, such as hydrophilic or lipophilic gelling agents, preservatives, antioxidants, solvents, perfumes, filler, sunscreen agents, odor absorbers and coloring mater. The amounts of these different adjuvants are those traditionally used in the cosmetic and/or pharmaceutical field, and are, for example from 0.1% to 10% of the total weight of the composition. The adjuvants, depending on their nature, may be introduced into the fatty phase, into the aqueous phase and/or into lipid spherules.

As oils which can be used in the invention, mineral oils, vegetable oils, animal oils, synthetic oils, silicone oils or waxes and fluorinated oils may be mentioned. Fatty alcohols and fatty acids may be added to these oils. Waxes such as beeswax and carnauba wax or paraffin may also be used.

As emulsifiers which can be used in the invention, glycerol stearate, polysorbate 60 and the PEG-6/PEG-32/glycol stearate, mixture sold under the name of Tefose 63 by the company Gattefosse may be mentioned as examples.

As solvents which can be used in the invention, lower alcohols, in particular ethanol and isopropanol, and propylene glycol may be mentioned.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids, such as aluminum stearates and hydrophobic silica may be mentioned.

It is, in addition, possible to introduce hydrophilic active agents such as proteins or protein hydrolysates, amino acids, polyols, urea, sugars, and sugar derivatives, vitamins, starch, plant extracts such as aloe vera and hydroxy acids such as lactic acid or tartaric acid.

It is also possible to introduce lipophilic active agents such as retinol and its derivatives, retinoids such as 13-cis- or all-trans-retinoic acid, tocopherol and its derivatives, essential fatty acids, ceramides, essential oils and salicylic acid and its derivatives. Salicylic, lactic, acetic and the like, acids act, in particular as antiseptics.

Pentapeptides isolated using the isolation method from the sea cucumber detailed below, or produced from direct peptide synthesis can be combined with pharmaceutical carriers to make novel dosage forms. These peptide based drugs trigger T-cell activation resulting in tumor inhibition. Effective dosages for the treatment of cancer include from 1 milligram per kilogram to 5000 milligrams per kilogram body weight of the individual in need of treatment.

The peptides of the invention also may be administered at a dose effective in inhibiting inflammation in the subject as determined using standard techniques. "Inhibiting inflammation" should be construed to refer to a significant decrease in the signs and symptoms of inflammation. For example, but not by way of limitation, symptomatic relief, in which a patient is rendered subjectively relieved of discomfort, would be considered as satisfactory results of therapy. In certain specific non-limiting embodiments, the amount of inflammation may be decreased by about 50%, the ED50 has been estimated to be a dose between about 1 and 40 mg/kg. In specific embodiments of the invention, the peptide may be administered to a human patient at a dose of about 2.5 mg/kg to about 500 mg/kg. In preferred, specific, non-limiting embodiments of the invention, the dose, administered topically to a human patient, may be either about 5 mg/kg, to 100 mg/kg, depending upon whether the inflammation to be treated is mild, moderate, or severe/persistent. The dose may be administered at appropriate intervals, e.g. but not limited to, daily, or once, twice, or three times a week. In another preferred, specific, non-limiting embodiment of the present invention, soft or hard gelatin capsules containing approximately 500 milligrams of the peptide are administered at approximately 30 mg/kg of body weight of an animal.

Angiogenesis related pathology in Rheumatoid Arthritis: The development of an extensive network of new blood vessels is essential to the development of the synovitis present in rheumatoid arthritis (Harris, 1990; Folkman et al., 1989; Sano et al., 1990). Several local mediators such as platelet derived growth factor (PDGF), TGF-.beta., and fibroblast growth factor (FGF) are likely responsible for the induction and perpetuation of neovascularization within the synovium. Pannus tissue composed of new capillaries and synovial connective tissue invades and destroys the articular cartilage. The migrating angiogenic vessels themselves produce and secrete increased levels of metalloproteinases such as collagenase and stromelysin capable of degrading the cartilage matrix (Case et al., 1989). The newly formed vessels are also quite "leaky" with gaps present between the microvascular endothelial cells. This facilitates the exudation of plasma proteins into the synovium (which increases swelling), enhances WBCs movement from the circulation into the pannus tissue (which increases inflammation), and leads to the perivascular accumulation of mononuclear inflammatory cells (Wilder et al., 1991). In summary, the endothelial tissue plays an important role in the development of this disease by expressing the necessary surface receptors to allow inflammatory cells to leave the circulation and enter the developing pannus, secreting proteolytic enzymes capable of degrading the cartilage matrix, and proliferating to form the new vessels (angiogenesis) required for the pannus tissue to increase in size and invade adjacent tissues. InflaStatin is contemplated to be injected into the synovium or articular spaces of joints of Rheumatoid arthritis patients whereby its anti-angiogenic effects will ameliorate the pathological angiogenesis activity therein.

Within one embodiment, inhibition of new blood vessel formation may be readily determined in a variety of assays, including the CAM assay described above.

NEOVASCULAR DISEASES OF THE EYE: As noted above, the present invention also provides methods for treating neovascular diseases of the eye, including for example, corneal neovascularization, neovascular glaucoma, proliferative diabetic retinopathy, retrolental fibroblasia and macular degeneration.

Briefly, corneal neovascularization as a result of injury to the anterior segment is a significant cause of decreased visual acuity and blindness, and a major risk factor for rejection of corneal allografts. As described by Burger et al., Lab, Invest. 48:169–180, 1983, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

Currently no clinically satisfactory therapy exists for inhibition of corneal neovascularization or regression of existing corneal new vessels. Topical corticosteroids appear to have some clinical utility, presumably by limiting stromal inflammation.

Thus, within one aspect of the present invention methods are provided for treating neovascular diseases of the eye such as corneal neovascularization (including corneal graft neovascularization), comprising the step of administering to a patient a therapeutically effective amount of an anti-angiogenic composition (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates.

Blood vessels can enter the cornea in a variety of patterns and depths, depending upon the process which incites the neovascularization. These patterns have been traditionally defined by ophthalmologists in the following types: pannus trachomatosus, pannus leprosus, pannus phylctenulosus, pannus degenerativus, and glaucomatous pannus. The corneal stroma may also be invaded by branches of the anterior ciliary artery (called interstitial vascularization) which causes several distinct clinical lesions: terminal loops, a "brush-like" pattern, an umbel form, a lattice form, interstitial arcades (from episcleral vessels), and aberrant irregular vessels.

A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

While the cause of corneal neovascularization may vary, the response of the cornea to the insult and the subsequent vascular ingrowth is similar regardless of the cause. Briefly, the location of the injury appears to be of importance as only those lesions situated within a critical distance of the limbus will incite an angiogenic response. This is likely due to the fact that the angiogenic factors responsible for eliciting the vascular invasion are created at the site of the lesion, and must diffuse to the site of the nearest blood vessels (the limbus) in order to exert their effect. Past a certain distance from the limbus, this would no longer be possible and the limbic endothelium would not be induced to grow into the cornea. Several angiogenic factors are likely involved in this process, many of which are products of the inflammatory response. Indeed, neovascularization of the cornea appears to only occur in association with an inflammatory cell infiltrate, and the degree of angiogenesis is proportional to the extent of the inflammatory reaction. Corneal edema further facilitates blood vessel ingrowth by loosening the corneal stromal framework and providing a pathway of "least resistance" through which the capillaries can grow.

Following the initial inflammatory reaction, capillary growth into the cornea proceeds in the same manner as it occurs in other tissues. The normally quiescent endothelial cells of the limbic capillaries and venules are stimulated to divide and migrate. The endothelial cells project away from their vessels of origin, digest the surrounding basement membrane and the tissue through which they will travel, and migrate towards the source of the angiogenic stimulus. The blind ended sprouts acquire a lumen and then anastomose together to form capillary loops. The end result is the establishment of a vascular plexus within the corneal stroma.

Anti-angiogenic factors and compositions of the present invention are useful by blocking the stimulatory effects of angiogenesis promoters, reducing endothelial cell division, decreasing endothelial cell migration, and impairing the activity of the proteolytic enzymes secreted by the endothelium.

Within particularly preferred embodiments of the invention, an anti-angiogenic factor may be prepared for topical administration in saline (combined with any of the preservatives and antimicrobial agents commonly used in ocular preparations), and administered in eyedrop form. The anti-angiogenic factor solution or suspension may be prepared in its pure form and administered several times daily. Alternatively, anti-angiogenic compositions, prepared as described above, may also be administered directly to the cornea, Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy.

Topical therapy may also be useful prophylactically in corneal lesions which are known to have a high probability of inducing an angiogenic response (such as chemical bums). In these instances the treatment, likely in combination with steroids, may be instituted immediately to help prevent subsequent complications.

Within other embodiments, the anti-angiogenic compositions described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. Asteroid could also be added to the injection solution to reduce inflammation resulting from the injection itself.

Within another aspect of the present invention, methods are provided for treating neovascular glaucoma, comprising the step of administering to a patient a therapeutically effective amount of an anti-angiogenic composition to the eye, such that the formation of blood vessels is inhibited.

Briefly, neovascular glaucoma is a pathological condition wherein new capillaries develop in the iris of the eye. The angiogenesis usually originates from vessels located at the pupillary margin, and progresses across the root of the iris and into the trabecular meshwork. Fibroblasts and other connective tissue elements are associated with the capillary growth and a fibrovascular membrane develops which spreads across the anterior surface of the iris. Eventually this tissue reaches the anterior chamber angle where it forms synechiae. These synechiae in turn coalesce, scar, and contract to ultimately close off the anterior chamber angle. The scar formation prevents adequate drainage of aqueous humor through the angle and into the trabecular meshwork, resulting in an increase in intraocular pressure that may result in blindness.

Neovascular glaucoma generally occurs as a complication of diseases in which retinal ischemia is predominant. In particular, about one third of the patients with this disorder have diabetic retinopathy and 28% have central retinal vein occlusion. Other causes include chronic retinal detachment, end-stage glaucoma, carotid artery obstructive disease, retrolental fibroplasia, sickle-cell anemia, intraocular tumors, and carotid cavernous fistulas. In its early stages, neovascular glaucoma may be diagnosed by high magnification slitlamp biomicroscopy, where it reveals small, dilated, disorganized capillaries (which leak fluorescein) on the surface of the iris. Later gonioscopy demonstrates progressive obliteration of the anterior chamber angle by fibrovascular bands. While the anterior chamber angle is still open, conservative therapies may be of assistance. However, once the angle closes surgical intervention is required in order to alleviate the pressure.

Therefore, within one embodiment of the invention anti-angiogenic factors (either alone or in an anti-angiogenic composition, as described above) may be administered topically to the eye in order to treat early forms of neovascular glaucoma.

Within other embodiments of the invention, anti-angiogenic compositions may be implanted by injection of the composition into the region of the anterior chamber angle. This provides a sustained localized increase of anti-angiogenic factor, and prevents blood vessel growth into the area. Implanted or injected anti-angiogenic compositions which are placed between the advancing capillaries of the iris and the anterior chamber angle can "defend" the open angle from neovascularization. As capillaries will not grow within a significant radius of the anti-angiogenic composition, patency of the angle could be maintained. Within other embodiments, the anti-angiogenic composition may also be placed in any location such that the anti-angiogenic factor is continuously released into the aqueous humor. This would increase the anti-angiogenic factor concentration within the humor, which in turn bathes the surface of the iris and its abnormal capillaries, thereby providing another mechanism by which to deliver the medication. These therapeutic modalities may also be useful prophylactically and in combination with existing treatments.

Within another aspect of the present invention, methods are provided for treating proliferative diabetic retinopathy, comprising the step of administering to a patient a therapeutically effective amount of an anti-angiogenic composition to the eyes, such that the formation of blood vessels is inhibited.

Briefly, the pathology of diabetic retinopathy is thought to be similar to that described above for neovascular glaucoma. In particular, background diabetic retinopathy is believed to convert to proliferative diabetic retinopathy under the influence of retinal hypoxia. Generally, neovascular tissue sprouts from the optic nerve (usually within 10 mm of the edge), and from the surface of the retina in regions where tissue perfusion is poor. Initially the capillaries grow between the inner limiting membrane of the retina and the posterior surface of the vitreous. Eventually, the vessels grow into the vitreous and through the inner limiting membrane. As the vitreous contracts, traction is applied to the vessels, often resulting in shearing of the vessels and blinding of the vitreous due to hemorrhage. Fibrous traction from scarring in the retina may also produce retinal detachment.

The conventional therapy of choice is panretinal photocoagulation to decrease retinal tissue, and thereby decrease retinal oxygen demands. Although initially effective, there is a high relapse rate with new lesions forming in other parts of the retina. Complications of this therapy include a decrease in peripheral vision of up to 50% of patients, mechanical abrasions of the cornea, laser-ihduced cataract formation, acute glaucoma, and stimulation of subretinal neovascular growth (which can result in loss of vision). As a result, this procedure is performed only when several risk factors are present, and the risk-benefit ratio is clearly in favor of intervention.

Therefore, within particularly preferred embodiments of the invention, proliferative diabetic retinopathy may be treated by injection of an anti-angiogenic factor(s) (or anti-angiogenic composition) into the aqueous humor or the vitreous, in order to increase the local concentration of anti-angiogenic factor in the retina. Preferably, this treatment should be initiated prior to the acquisition of severe disease requiring photocoagulation. Within other embodiments of the invention, arteries which feed the neovascular lesions may be embolized (utilizing anti-angiogenic compositions, as described above)

Within another aspect of the present invention, methods are provided for treating retrolental fibroblasia, comprising the step of administering to a patient a therapeutically effective amount of an anti-angiogenic factor (or anti-angiogenic composition) to the eye, such that the formation of blood vessels is inhibited.

Briefly, retrolental fibroblasia is a condition occurring in premature infants who receive oxygen therapy. The peripheral retinal vasculature, particularly on the temporal side, does not become fully formed until the end of fetal life. Excessive oxygen (even levels which would be physiologic at term) and the formation of oxygen free radicals are thought to be important by causing damage to the blood vessels of the immature retina. These vessels constrict, and then become structurally obliterated on exposure to oxygen. As a result, the peripheral retina fails to vascularize and retinal ischemia ensues. In response to the ischemia, neovascularization is induced at the junction of the normal and the ischemic retina.

In 75% of the cases these vessels regress spontaneously. However, in the remaining 25% there is continued capillary growth, contraction of the fibrovascular component, and traction on both the vessels and the retina. This results in vitreous hemorrhage and/or retinal detachment which can lead to blindness. Neovascular angle-closure glaucoma is also a complication of this condition.

As it is often impossible to determine which cases will spontaneously resolve and which will progress in severity, conventional treatment (i.e., surgery) is generally initiated only in patients with established disease and a well developed pathology. This "wait and see" approach precludes early intervention, and allows the progression of disease in the 25% who follow a complicated course. Therefore, within one embodiment of the invention, topical administration of anti-angiogenic factors (or anti-angiogenic compositions, as described above) may be accomplished in infants which are at high risk for developing this condition in an attempt to cut down on the incidence of progression of retrolental fibroplasia. Within other embodiments, intravitreous injections and/or intraocular implants of an anti-angiogenic composition may be utilized. Such methods are particularly preferred in cases of established disease, in order to reduce the need for surgery.

OTHER THERAPEUTIC USES OF ANTI-ANGIOGENIC INFLASTATIN: Anti-angiogenic factors and compositions of the present invention may be utilized in a variety of additional methods in order to therapeutically treat a cancer or tumor. For example, anti-angiogenic factors or compositions described herein may be formulated for topical delivery, in order to treat cancers such as skin cancer, head and neck tumors, breast tumors, and Kaposi's sarcoma. Within yet other aspects, the anti-angiogenic factors or compositions provided herein may be utilized to treat superficial forms of bladder cancer by, for example, intravesical administration.

In addition to cancer, however, numerous other non-tumorigenic angiogenesis-dependent diseases which are characterized by the abnormal growth of blood vessels may also be treated with the anti-angiogenic factors or compositions of the present invention. Representative examples of such non-tumorigenic angiogenesis-dependent diseases include hypertrophic scars and keloids, proliferative diabetic retinopathy (discussed above), rheumatoid arthritis (discussed above), arteriovenous malformations (discussed above), atherosclerotic plaques, delayed wound healing, hemophilic joints, nonunion fractures, Osier-Weber syndrome, psoriasis, pyogenic granuloma, scleroderma, tracoma, menorrhagia (discussed above) and vascular adhesions.

For example, within one aspect of the present invention methods are provided for treating hypertrophic scars and keloids, comprising the step of administering one of the above-described anti-angiogenic compositions to a hypertrophic scar or keloid.

Briefly, healing of wounds and scar formation occurs in three phases: inflammation, proliferation, and maturation. The first phase, inflammation, occurs in response to an injury which is severe enough to break the skin. During this phase, which lasts 3 to 4 days, blood and tissue fluid form an adhesive coagulum and fibrinous network which serves to bind the wound surfaces together. This is then followed by a proliferative phase in which there is ingrowth of capillaries and connective tissue from the wound edges, and closure of the skin defect. Finally, once capillary and fibroblastic proliferation has ceased, the maturation process begins wherein the scar contracts and becomes less cellular, less vascular, and appears flat and white. This final phase may take between 6 and 12 months.

If too much connective tissue is produced and the wound remains persistently cellular, the scar may become red and raised. If the scar remains within the boundaries of the original wound it is referred to as a hypertrophic scar, but if it extends beyond the original scar and into the surrounding tissue, the lesion is referred to as a keloid. Hypertrophic scars and keloids are produced during the second and third phases of scar formation. Several wounds are particularly prone to excessive endothelial and fibroblastic proliferation, including bums, open wounds, and infected wounds. With hypertrophic scars, some degree of maturation occurs and gradual improvement occurs. In the case of keloids however, an actual tumor is produced which can become quite large. Spontaneous improvement in such cases rarely occurs.

Therefore, within one embodiment of the present invention either anti-angiogenic factors alone, or anti-angiogenic compositions as described above, are directly injected into a hypertrophic scar or keloid, in order to prevent the progression of these lesions. The frequency of injections will depend upon the release kinetics of the polymer used (if present), and the clinical response. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development.

As noted above, within yet another aspect of the present invention, vascular grafts are provided comprising a synthetic tube, the surface of which is coated with an anti-angiogenic composition as described above. Briefly, vascular grafts are synthetic tubes, usually made of Dacron or Gotrex, inserted surgically to bypass arterial blockages, most frequently from the aorta to the femoral, or the femoral to the popliteal artery. A major problem which particularly complicates femoral-popliteal bypass grafts is the formation of a subendothelial scar-like reaction in the blood vessel wall called neointimal hyperplasia, which narrows the lumen within and adjacent to either end of the graft, and which can be progressive. A graft coated with or containing anti-angiogenic factors (or anti-angiogenic compositions, as described above) may be utilized to limit the formation of neointimal hyperplasia at either end of the graft. The graft may then be surgically placed by conventional bypass techniques.

Anti-angiogenic compositions of the present invention may also be utilized in a variety of other manners. For example, they may be incorporated into surgical sutures in order to prevent stitch granulomas, implanted in the uterus (in the same manner as an IUD) for the treatment of menorrhagia or as a form of female birth control, administered as either a peritoneal lavage fluid or for peritoneal implantation in the treatment of endometriosis, attached to a monoclonal antibody directed against activated endothelial cells as a form of systemic chemotherapy, or utilized in diagnostic imaging when attached to a radioactively labeled monoclonal antibody which recognizes activated endothelial cells.

Anti-microbial. The pentapeptide of the present invention is also thought to be an inhibitor of various gram negative and gram positive bacteria and certain viruses, and as such, is suitable at various dosages as a medical therapeutic in the amelioration of mammalian diseases in which bacteria or viruses contribute to the pathological condition.

Peptide Production: The peptide of the present invention was first isolated from the epithelia of a sea cucumber body wall, and can be derived from any species or subphyla of sea cucumber. The peptide can be isolated from the epithelial layer of any sea cucumber, prepared as described in U.S. Pat. No. 5,770,205 by Collin (incorporated herein by reference). It is an object of the present invention to further elucidate the anti-cancer activity of sea cucumber tissues. The methods to prepare isolated sea cucumber epithelial layer are as follows:

The anterior, posterior, viscera and muscles were removed from sea cucumber of the species *Cucumaria frondosa* to obtain an isolated body wall. Body wall portions thus obtained were heated from about 30 minutes in fresh 170 degree F. water, then cooled on wire racks to room temperature. Next, the body wall portions were passed through an industrial machine known to those in the food processing arts as a deboner or mincer (Paoli Machine, III). The deboner was adjusted to separate the softer outer epithelial layer from the harder collagenous portion of the body wall. The black viscous layer of the epithelium so separated, was dried by conventional means using a 40 hp "heat pump" dryer (SouthWind, Nova Scotia, CN) to approximately 5 percent moisture content and finely divided to obtain a powder. Any method whereby the softer epithelial layer is separable from the inner collagenous layer is suitable to produce the raw material from which the peptide of the present invention is derived. The epithelial layer can also be kept frozen and not dried after separation from the skin of any sea cucumber. It is also possible to produce the peptide of the present invention from sea cucumber body wall which has not had epithelia separated from it, but the percentage of recovery via that method is extremely low and can be contaminated by different and non-active peptides of the same or similar length.

Figure 2:
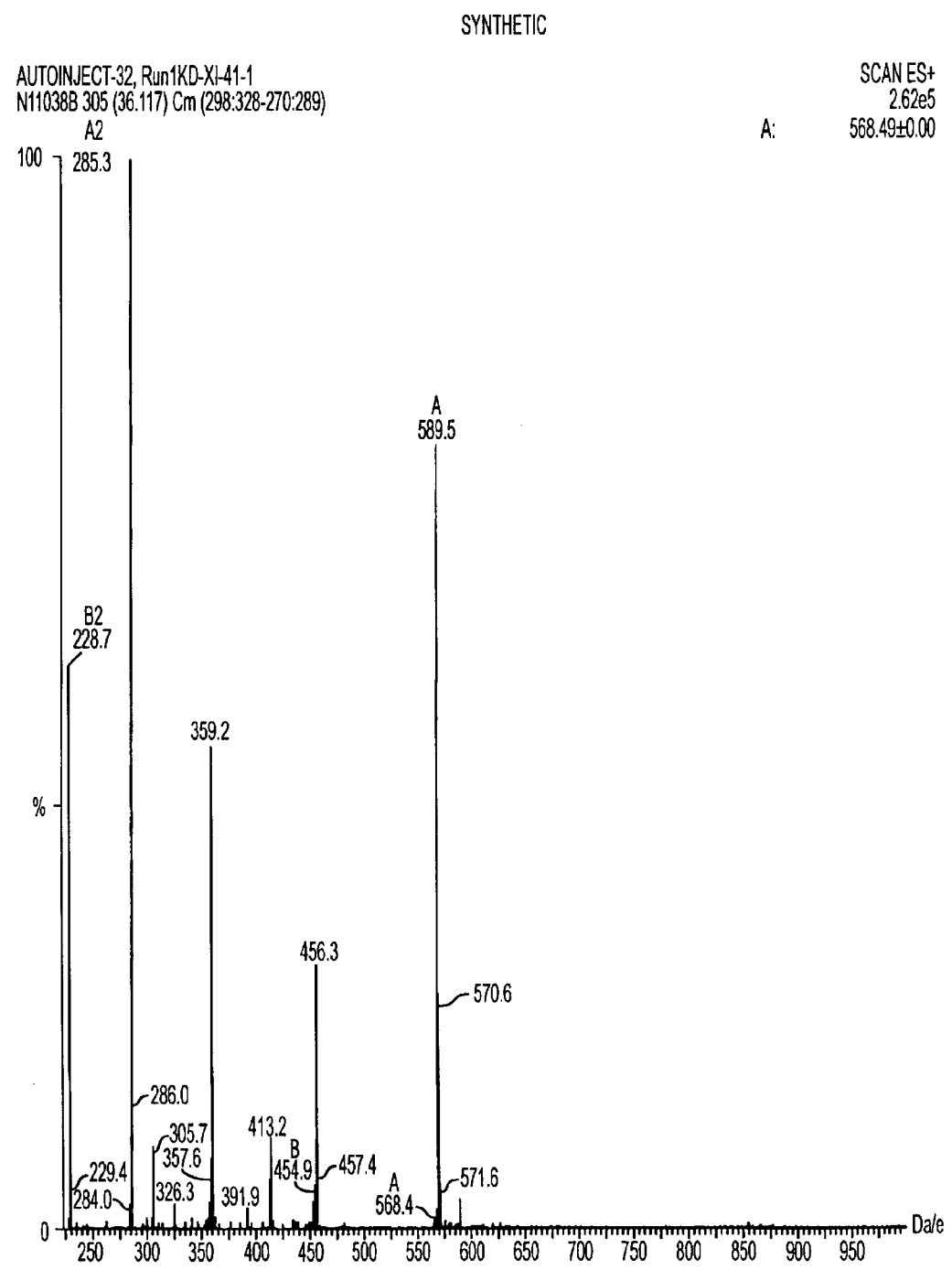
FIG. 2 shows the mass spectrum of a synthetic preparation of the peptide of SEQ. ID NO. 1.
Figure 3:
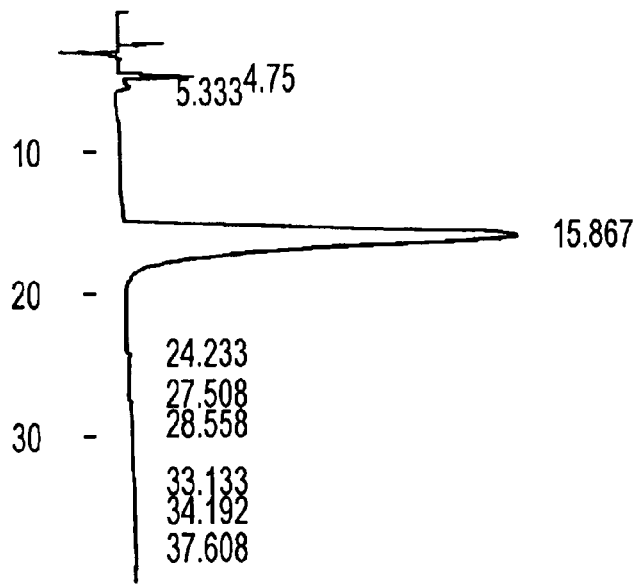
FIG. 3 shows an HPLC trace indicating the purity of the synthetic peptide preparation.

The frozen or dried epithelial layer (1 kg) was ground up and extracted with one liter of hexane. The hexane was removed and residue then extracted with one liter of acetone. The acetone and hexane extracts were combined and the solvents were removed by distillation. The remainder of the material (pulp) was mixed with ½ liter of water and the pH was adjusted to 9.0 using sodium hydroxide (100 ml, 5N), stirred and then extracted with one liter of ethyl acetate followed by one liter of normal butanol. The solvent fractions were combined and taken to dryness at 45 degrees C. with a rotary evaporation with a partial vacuum. This fraction contained the peptide of the present invention. The residue was dissolved in normal butanol, treated with norite and filtered to remove a pigment. The material was recrystallized by solvent removal. The yield of peptide is 60 milligrams from a starting material weight of 1 kilogram. The resulting material is a white crystalline material. The amino acid analysis shows it to be made up of leucine, proline arginine, and serine. Optical rotation C=1, H2O [alpha] 0=125 degrees. Water content of one sample was 2 percent. A mass spectroscopy spectrum of the purified peptide is shown in FIG. 1. The peptides of the present invention can also be prepared using standard peptide synthesis techniques known in the art. A mass spectrum of a synthetic preparation of the peptide of SEQ. ID NO. 1 is shown in FIG. 2. An HPLC trace indicating the purity of the preparation appears in FIG. 3.

Accordingly, it is an object of the present invention to provide a compound and method to inhibit unwanted angiogenesis in a human or animal.

It is yet another object of the present invention to provide a composition of inhibiting angiogenesis by oral administration of the composition.

It is another object of the present invention to provide a treatment for diseases mediated by angiogenesis.

It is yet another object of the present invention to provide a treatment for macular degeneration.

It is yet another object of the present invention to provide a treatment for all forms of proliferative vitreoretinopathy including those forms not associated with diabetes.

It is yet another object of the present invention to provide a treatment for solid tumors.

It is yet another object of the present invention to provide a method and composition for the treatment of blood-born tumors such as leukemia.

It is another object of the present invention to provide a method and composition for the treatment of hemangioma.

It is another object of the present invention to provide a method and composition for the treatment of retrolental fibroplasia.

It is another object of the present invention to provide a method and composition for the treatment of psoriasis.

It is another object of the present invention to provide a method and composition for the treatment of Kaposi's sarcoma.

It is another object of the present invention to provide a method and composition for the treatment of Crohn's diseases and other inflammatory bowel disease.

It is another object of the present invention to provide a method and composition for the treatment of diabetic retinopathy.

Other features and advantages of the invention will be apparent from the following description of preferred embodiments thereof.

EXAMPLE 1

Peptide Production

The peptide of the present invention was first isolated from the epithelia of a sea cucumber body wall, and can be derived from any species or subphyla of sea cucumber. The peptide can be isolated from the epithelial layer of any sea cucumber, prepared as described in U.S. Pat. No. 5,770,205 by Collin (incorporated herein by reference). The methods to prepare isolated sea cucumber epithelial layer are as follows:

The anterior, posterior, viscera and muscles were removed from seq cucumber of the species *Cucumaria frondosa* to obtain an isolated body wall. Body wall portions thus obtained were heated from about 30 minutes in fresh 170 degree F. Water, then cooled on wire racks to room temperature. Next, the body wall portions were passed through an industrial machine known to those in the food processing arts as a deboner or mincer (Paoli Machine, III). The deboner was adjusted to separate the softer outer epithelial layer from the harder collagenous portion of the body wall. The black viscous layer of the epithelium so separated, was dried by conventional means using a 40 hp "heat pump" dryer (SouthWind, Nova Scotia, CN) to approximately 5 percent moisture content and finely divided to obtain a powder. Any method whereby the softer epithelial layer is separable from the inner collagenous layer is suitable to produce the raw material from which the peptide of the present invention is derived. The epithelial layer can also be kept frozen and not dried after separation from the skin of any sea cucumber. It is also possible to produce the peptide of the present invention from sea cucumber body wall which has not had epithelia separated from it, but the percentage of recovery via that method is extremely low and can be contaminated by different and non-active peptides of the same or similar length.

The frozen epithelial layer (1 kg) was ground up and extracted with one liter of hexane. The hexane was removed and residue then extracted with one liter of acetone. The acetone and hexane extracts were combined and the solvents were removed by distillation. The remainder of the material (pulp) was mixed with ½ liter of water and the pH was adjusted to 9.0 using sodium hydroxide (100 ml, 5N), stirred and then extracted with one liter of ethyl acetate followed by one liter of normal butanol. The solvent fractions were combined and taken to dryness at 45° C. with a rotary evaporation with a partial vacuum. This fraction contained the peptide of the present invention. The residue was dissolved in normal butanol, treated with norite and filtered to remove pigment. The material was recrystallized by solvent removal. The yield of peptide was 60 milligrams from a starting material weight of 1 kilogram. The resulting material is a white crystalline material.

Amino acid analysis shows the peptide to be made up of leucine, proline arginine, and serine. Optical rotation C=1, H2O [alpha] 0=125 degrees. Water content of one sample was 2 percent. A mass spectroscopy spectrum of the purified peptide is shown in FIG. 1.

The peptides of the present invention can also be prepared using standard peptide synthesis techniques known in the art. A mass spectrum of a synthetic preparation of the peptide of SEQ. ID NO. 1 is shown in FIG. 2. An HPLC trace indicating the purity of the preparation appears in FIG. 3.

EXAMPLE 2

In Vivo Anti-Inflammatory Activity

The anti-inflammatory activity of the isolated peptide of Example 1 was tested by oral administration to rats in an Adjuvant Induced Arthritis assay and by a Mouse Ear Edema assay, as are known in the arts.

Adjuvant Induced Arthritis Model: Male Sprague-Dawley rats (160–180 g) were sensitized by injecting Fruend's Complete Adjuvant (0.5% suspension of killed mycobacterium tuberculosis (H37RA, Difco in mineral oil)). 0.05 ml was administered intradermally at a plantar site on the right hind leg of each rat. The test materials were given orally (by gavage) in 0.5% methylcelluose, at a dose level of 20 milligrams per kilo body weight, and given once per day for 14 days. The administration was started the day after sensitization. The left hind paw was measured just before sensitization and on Day 14, and the plantar edema inhibitory rate and the body weight gain rate were determined in comparison with the nonsensitized rat groups. The paw weights for each group in each test run were averaged. Activity was calculated as follows:

$$\frac{\text{Mean paw weights of controls-Mean paw weights of test group}}{\text{Mean paw weights of test group}} \times 100 =$$

% anti-inflammatory response

Figure 4:
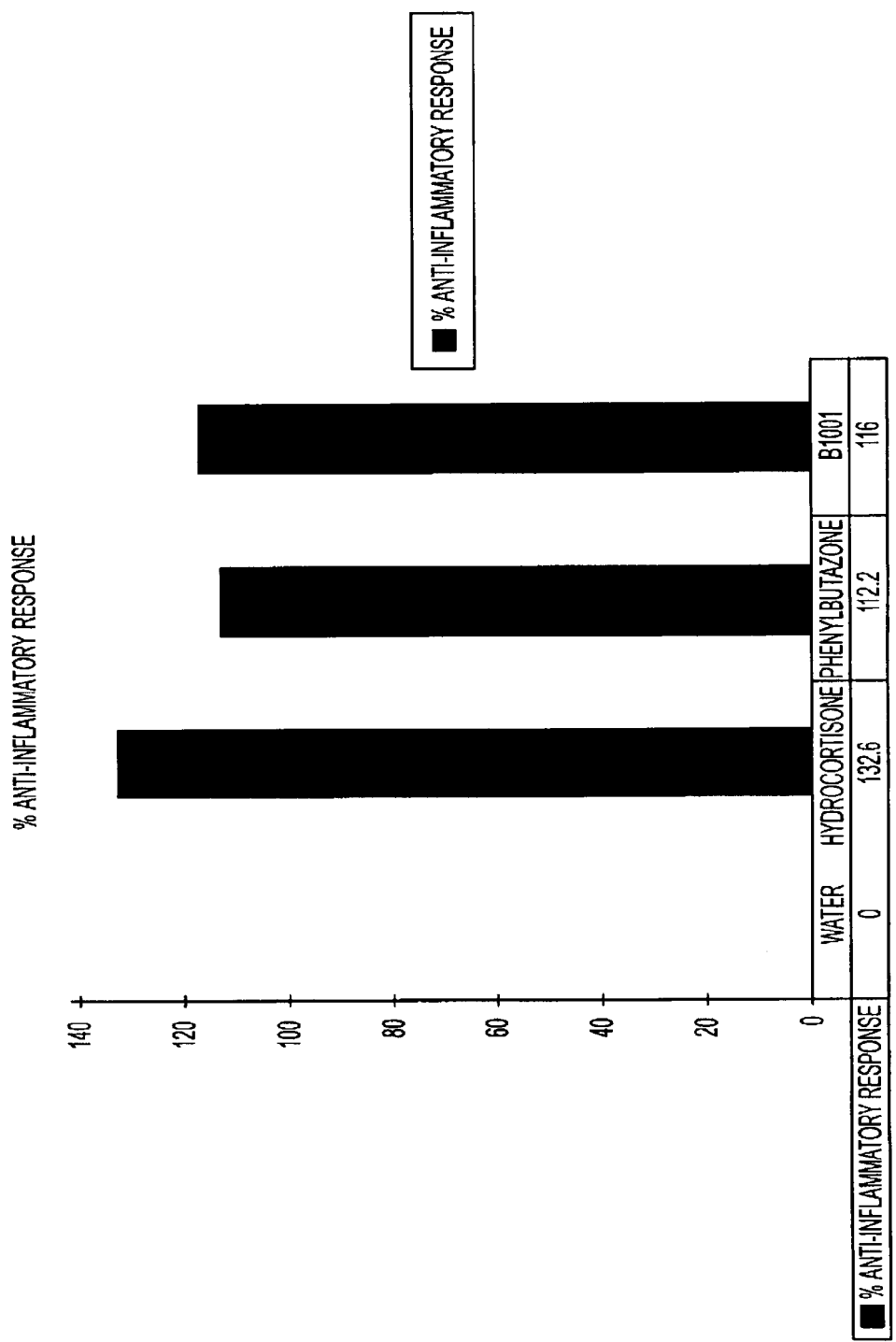
FIG. 4 shows the anti-inflammatory response of the peptide Adjuvant Induced Arthritis Model.

The Anti-inflammatory response is the difference in the mean foot volume. This is also calculated as a "percent inhibition." Phenylbutazone and hydrocortisone assayed concurrently with InflaStatin and the same 20 mg per KG body weight gave responses of 112.2% and 132.6% respectively while the peptide of the present invention gave an anti-inflammatory response of 116.3%. FIG. 4.

Mouse-ear edema model. Croton-oil, which contains a variety of phorbol esters, and arachidonic acid (AA) are standard inducers of inflammation in mouse ears when applied topically. Phorbol esters, especially phorbol myristyl acetate (PMA), activate one or more isozymes of the ubiquitous membrane receptor, protein kinase C (PKC), which in turn initiates several metabolic cascades leading to inflammation. As is a substrate for one of these cascades, leading to prostaglandin and leukotriene production, both of which are inflammatory. Inhibition of such inflammation by a putative bioactive agent is considered a generalized indicator of potential pharmacologic activity.

Male Swiss Webster mice (15–20 g) were purchased from B&K Universal, Kent, Wash. and maintained in the laboratory for one day prior to entering the experiment. At t=0, the ventral side of both ears of each mouse was challenged topically with 10 λ of 10% croton oil in acetone. At t=30 min, the same pinnal area was treated topically with 20 λ of either carbopol (n=2 ears) or 5% peptide dissolved in carbopol (n=4 ears). The animals were sacrificed by cervical dislocation at t=24 hrs, the ears removed, and a biopsy take from each ear with an 8 mm punch. The biopsy was immediately weighed on a 4-place balance. Results showed that the peptide of the present invention produced a 61% reduction in swelling compared to vehicle-only treated ears.

EXAMPLES 3–9

In Vitro Activities

A variety of activities of the peptide of Example 1 were tested in a range of in vitro assays.

I. MATERIALS AND EQUIPMENT

A. Test Substances and Dosing Pattern

Peptide was prepared according to the methods set out in Example 1. The vehicle of distilled water was used for in vitro assays, working solution of peptide was added to the 10 ml tissue bath. For in vivo assay, distilled water and saline was used as vehicle in oral and intraperitoneal administration, respectively. Dosing volume was 20 ml/kg for mice or 10 ml/kg for rats. For topical route, peptide was dissolved in a vehicle of Acetone/Ethanol (1:1) and applied in a dosing volume 20 µl/ear.

B. Chemicals

Aluminum Hydroxide (Sigma, U.S.A.), Acetone (Wako, Japan), BSA (Bovine Serum Albumin), $CaCl_2$ (Merck, Germany), Croton Oil (Sigma, U.S.A.), Cyclophosphamide Monohydrate (Sigma, U.S.A.), DNBS (2,4-Dinitrobenzenesulfonic Acid, TCI, Japan), Dimethyl Sulfoxide (Mark, Germany), Ethanol (Merck, Germany), Galanin (Sigma, U.S.A.), (+)Glucose (Sigma, U.S.A.), Histamine-diphosphate (Sigma, U.S.A.), Indomethacin (Sigma, U.S.A.), KCl (Wako, Japan), $KH_2PO_4$ (Wako, Japan), $MgSO_4 7H_2O$ (Wako, Japan), Mepyramine Maleate (Sigma, U.S.A.), $NaHCO_3$ (Merck, Germany), NaCl (Merck, Germany), Ovalbumin (Sigma, U.S.A.), Oxazolone (Sigma, U.S.A.), PAF (Sigma, U.S.A.), Pentobarbital Sodium (Tokyo Kasei, Japan), Propranolol-HCl (Sigma, U.S.A.), Pyrogen-Free Saline (Astar, Taiwan), Pyrilamine Maleate (Sigma, U.S.A.), R-α-Methyl histamine (RBI, U.S.A.), Succinylcholine Chloride (Asta-Werke, Bielefeld, Germany), Sulfasalazine (Sigma, U.S.A.), WEB 2086 (Boehringer Ingelheim). Doses for compounds in salt form were calculated on the basis of the weight of the salt.

C. Equipment

Dyer model micrometer gauge (Peacock, Japan), EKG: Cardionec (NEC San-ei, Japan), Isotonic transducer # 50–6360 (Harvard, U.S.A.), 2-pen recorder SS-250F (Sekonic, Japan), Micropipet # P20, P200 and P1000 (Gilson, U.S.A.), Mouse scale Z-40 (Taconic), Pen oscillograph Type 8K (NEC San-ei, Japan), Pressure transducer # P23xL (Viggo-Spectramed, U.S.A.), Pneumatic pulse transducer (Narco, U.S.A.), Rodent ventilator # 683 (Harvard, U.S.A.), Recorder # SS-250 (Sekonic, Japan), Transducer amplifier # 50–7970 (Harvard, U.S.A.).

D. Animals

In these studies, male/female Wistar derived rats, male Sprague-Dawley derived rats, male/female Duncan Hartley derived guinea pigs and male ICR derived mice provided by MDS Panlabs Taiwan, Ltd. were used. Space allocation for animals was as follows: 45×23×15 cm for 10 mice, 45×23×15 cm for 6 rats and 43×21×20 cm for 3 guinea pigs. The animals were housed in APECR (Allentown Gaging, Allentown, N.J. 08501, U.S.A.) cages. Free access to standard lab chow (Fwusow Industry Limited Co., Taiwan) and tap water was granted. All animals were maintained in a controlled temperature (22°–24° C.) and humidity (60%–80%) environment with 12 hour light dark cycles for at least one week in Panlabs laboratory prior to use. All aspects of this work including housing, experimentation an d disposal of animals were performed in general according to the International Guiding Principles for Biomedical Research Involving Animals (CIOMS Publication No. ISBN 92 90360194, 1985).

Total Tested Animals: 45 mice and 9 rats and 9 guinea pigs

Total Tested Tissues: 4

II. METHODS AND RESULTS

EXAMPLE 3

Galanin Agonism/Antaonism

A segment of ileum obtained from Wistar derived male or female rats weighing 275±25 gms and sacrificed by $CO_2$ overexposure was used. The tissue was placed under 1 g tension in a 10 ml bath containing Kreb's solution pH 7.4 at 32° C. Test substance (30 μM)-induced contraction 50 percent or more (≧50%) within 5 minutes, relative to control 0.1 μM galanin response, indicated possible galanin receptor agonist activity. Atha test substance concentration where no significant agonist activity was seen, ability to reduce the galanin-induced contractile response bys o percent or more (≧50%) indicated galanin receptor antagonist activity. Each concentration was tested on two separate preparations. The results are set forth below in Table 1.

TABLE 1

Galanin Agonism/Antagonism

| Compound | Route | Conc. | N | Agonism | Antagonism |
|---|---|---|---|---|---|
| Vehicle | in vitro | 0.1 ml | 1 | 0 | 0 |
| (Distilled Water) | in vitro | 0.1 ml | 1 | 0 | 0 |
|  |  | Ave. |  | 0 | 0 |
| Peptide | in vitro | 30 μM | 1 | 0 | 24 |
|  | in vitro | 30 μM | 1 | 0 | 0 |
|  |  | Ave. |  | 0 | 12 |
| Galanin | in vitro | 0.1 μM | 1 | 100 | ND |
|  | in vitro | 0.1 μM | 1 | 100 | ND |
|  |  | Ave. |  | 100 | ND |

A segment of rat ileum was placed under 1 g tension in a 10 ml bath Krebs solution pH 7.4 at 32° C. Test substance-induced isotonically recorded contraction within 5 minutes indicated agonist activity. The ability to reduce the 0.1 μM galanin-induced contractile response indicated antagonist activity. ND: Not determined because agonist activity was significant.
Total tested tissues in this assay: 2

EXAMPLE 4

Histamine $H_3$ Agonism/Antagonism

A segment of ileum obtained from Duncan Hartley derived male or female guinea pigs weighing 325±25 gms and sacrificed by $CO_2$ overexposure were used. The tissue was placed under 0.5 g tension in a 10 ml bath containing Kreb's solution pH 7.4 and pyrilamine (0.3 μM) at 32° C. and subjected to field stimulation (70% of maximum voltage, 0.1 Hz, 0.5 millisecond). Test substance (30 μM)-induced reduction of isometrically recorded contractions 50 percent or more (≧50%) within 5 minutes, relative to control 0.3 μM R-α-methylhistamine response, indicated possible histamine $H_3$ receptor agonist activity. At a test substance concentration where no significant agonist activity was seen, ability to inhibit R-α-methylhistamine-induced response by 50 percent or more (≧50%) indicated histamine $H_3$ receptor antagonist activity. Each concentration was tested on two separate preparations. The results are set forth below in Table 2.

TABLE 2

Histamine $H_3$ Agonism/Antagonism

| Compound | Route | Conc. | N | Agonism | Antagonism |
|---|---|---|---|---|---|
| Vehicle | in vitro | 0.1 ml | 1 | 0 | 0 |
| (Distilled Water) | in vitro | 0.1 ml | 1 | 0 | 0 |
|  |  | Ave. |  | 0 | 0 |
| Peptide | in vitro | 30 μM | 1 | 4 | 0 |
|  | in vitro | 30 μM | 1 | 0 | 7 |
|  |  | Ave. |  | 4 | 4 |
| R (α)-Methylhistamine | in vitro | 0.3 μM | 1 | 100 | ND |
|  | in vitro | 0.1 μM | 1 | 100 | ND |
|  |  | Ave. |  | 100 | ND |
| Thioperamide | in vitro | 0.3 μM | 1 | 0 | 90 |
|  | in vitro | 0.3 μM | 1 | 0 | 96 |
|  |  | Ave. |  | 0 | 93 |

A segment of guinea pig ileum was placed under 0.5 g tension and subjected to field stimulation in a 10 ml bath Krebs solution pH 7.4 at 32° C. Test substance-induced isometrically recorded relaxation within 5 minutes indicated agonist activity. The ability to reduce the 0.3 μM R(α)-methylhistamine-induced relaxation response indicated antagonist activity. ND: Not determined because agonist activity was significant.
Total tested tissues in this assay: 2

EXAMPLE 5

Immune Suppression, Cellular

Groups of 5 ICR derived male mice weighing 22±1 gms were used. The preshaved abdominal surface was sensitized by application of oxazolone 0.1 ml of 5% solution. Test substance of peptide at dose of 100 mg/kg and vehicle (saline) were administered into the mice intra peritoneally after one hour and daily for five consecutive doses. After additional four days, the animals were challenged by secondary application of oxazolone (0.025 ml of 5% solution) to the right ear. After a further 24 hours, each mouse was sacrificed and ear thickness measured with a Dyer Model micrometer gauge. A 30 percent or more ($\geq 30\%$) decrease relative to the vehicle control group was considered significant and indicated possible immunosuppressant activity. The results are set forth in Table 3, below.

TABLE 3

Immune, Suppression, Cellular

| Compound | Route | Dose | N | Thickness (x 0.1 mm) R. Ear | L. Ear | Net | % INH |
|---|---|---|---|---|---|---|---|
| Vehicle-control (Saline) | IP | 20 ml/kg × 5 | 1 | 52 | 20 | 32 | |
| | IP | 20 ml/kg × 5 | 2 | 53 | 22 | 31 | |
| | IP | 20 ml/kg × 5 | 3 | 47 | 22 | 25 | |
| | IP | 20 ml/kg × 5 | 4 | 45 | 22 | 23 | |
| | IP | 20 ml/kg × 5 | 5 | 50 | 23 | 27 | |
| | | | X | | | 27.6 | 0 |
| | | | SEM | | | 1.7 | |
| Peptide | IP | 100 mg/kg × 5 | 1 | 43 | 23 | 20 | |
| | IP | 100 mg/kg × 5 | 2 | 43 | 22 | 21 | |
| | IP | 100 mg/kg × 5 | 3 | 44 | 20 | 24 | |
| | IP | 100 mg/kg × 5 | 4 | Died | Died | Died | |
| | IP | 100 mg/kg × 5 | 5 | 50 | 23 | 27 | |
| | | | X | | | 23.0 | 17 |
| | | | SEM | | | 1.6 | |
| Cyclo-phosphamide | IP | 30 mg/kg × 5 | 1 | 38 | 22 | 16 | |
| | IP | 30 mg/kg × 5 | 2 | 26 | 16 | 10 | |
| | IP | 30 mg/kg × 5 | 3 | 32 | 18 | 14 | |
| | IP | 30 mg/kg × 5 | 4 | 23 | 16 | 7 | |
| | IP | 30 mg/kg × 5 | 5 | 40 | 20 | 20 | |
| | | | X | | | 13.4 | 51 |
| | | | SEM | | | 2.3 | |

Test compound was administered IP in groups of 5 mice one hour after sensitization and daily for five consecutive doses. The challenge of oxazolone was applied on day 8 and the ear thickness was recorded 24 hours later. One animal out of 5 tested animals died on day 8 before oxazolone application.
Total tested animals in this assay: 15 mice

EXAMPLE 6

Inflammation, Inflammatory Bowel Disease

Groups of 3 Sprague-Dawley derived male rats weighing 150±20 gms and fasted for 24 hours were used. Distal colitis was induced by intra-colonic instillation of DNBS (2,4-dinitrobenzene sulfonic acid, 30 mg in 0.5 ml ethanol 30%) after which air (2 ml) was gently injected through the cannula to ensure that the solution remains in the colon. Test substance was administered PO (30 mg/kg) at 24 and 2 hours before DNBS instillation. Then, the animals received test compound every 24 hours for 5 consecutive days. The control group was given vehicle alone as compound dosing pattern. The animals were sacrificed 24 hours after the final dose of test compound administration and each colon was removed and weighed. Colon-to-body weight ratio was obtained from the percentage of the comparison between the animal colon weight and body weight on the $8^{th}$ day. A 30 percent or more ($\pm 30\%$) reduction in colon-to-body weight ratio relative to the vehicle treated control group was considered significant. The results are set forth in Table 4, below.

TABLE 4

Inflammation, Inflammatory Bowel Disease

| Compound | Route | Dose | No. | Ratio Ind. | Net | % INH. |
|---|---|---|---|---|---|---|
| Blank-control | — | — | 1 | 0.406 | | |
| | | | 2 | 0.353 | | |
| | | | 3 | 0.352 | | |
| | | | X | 0.370 | — | — |
| | | | SEM | 0.018 | | |
| Vehicle-control (Distilled Water) | PO | 10 ml/kg × 7 | 1 | 0.672 | | |
| | PO | 10 ml/kg × 7 | 2 | 0.768 | | |
| | PO | 10 ml/kg × 7 | 3 | 0.736 | | |
| | | | X | 0.725 | 0.355 | 0 |
| | | | SEM | 0.028 | | |
| Peptide | PO | 30 mg/kg × 7 | 1 | 0.683 | | |
| | PO | 30 mg/kg × 6 | 2 | Died | | |
| | PO | 30 mg/kg × 7 | 3 | 0.608 | | |
| | | | X | 0.646 | 0.276 | 22 |
| | | | SEM | 0.038 | | |
| Sulfasalazine | PO | 300 mg/kg × 7 | 1 | 0.496 | | |
| | PO | 300 mg/kg × 7 | 2 | 0.508 | | |
| | PO | 300 mg/kg × 7 | 3 | 0.650 | | |
| | | | X | 0.551 | 0.181 | 49 |
| | | | SEM | 0.050 | | |

Test substance was administered PO (30 mg/kg) at 24 and 2 hours before DNBS instillation and then daily for 5 days. Groups of 3 tested rats were sacrificed hours after the final compound administration. The colon-to-body weight ratio was recorded. Ratio: Colon (g)/$8^{th}$ B.W. × 100%. One out of 7 tested animals died on day 7 after daily compound administration.
Total tested animals in this assay: 9 rats

EXAMPLE 7

Platelet Activating Factor (PAF) Antagonism

Groups of 5 male ICR mice weighing 22±2 gms were employed. At dose of 100 mg/kg test substance dissolved in a vehicle of distilled water were administered orally. The control group received vehicle alone. At 60 minutes after dosing, the animals were injected intravenously PAF-acether (100 µ/kg IV, dissolved in 0.25% BSA). One hour later, the survival animals were recorded. The prevention of PAF-induced mortality in 50 percent or more ($\geq 50\%$) of mice indicated significant activity. The results are set forth in Table 5, below.

TABLE 5

Platelet Activating Factor (PAF) Antagonism

| Compound | Route | Dose | N | No. of Survival | % Protection |
|---|---|---|---|---|---|
| Vehicle (2% Tween 80) | PO | 20 ml/kg | 5 | 0 | 0 |
| Peptide | PO | 100 mg/kg | 5 | 0 | 0 |
| WEB-2086 | PO | 3 mg/kg | 5 | 3 | 60 |

Test compound was administered PO (100 mg/kg) to a group of 5 mice at one hour before injection of PAF-acether (100 µg/kg IV), then the number of survival was recorded.
Total tested animals in this assay: 15 mice

EXAMPLE 8

Pulmonary, Histamine $H_3$

A group of Duncan Hartley derived male or female guinea pigs weighing 250±50 gms were anesthetized with pentobarbital sodium (50 mg/kg IP plus an additional 15 mg/kg IP if required) and succinylcholine chloride (2 mg/animal IP) was subsequently administered to prevent spontaneous respiration. Body temperature was maintained at 37° to 38° C. The trachea was cannulated and the guinea pig ventilated with a Harvard rodent respirator in a closed system. Tracheal pressure (TP) was recorded through a side-arm of the cannula connected to a P23ID Statham transducer. Respiratory rate set at 50 strokes/minute with a stroke volume (approximately 1 ml/100 g) sufficient to produce a baseline tracheal pressure of 6 cm $H_2O$. Mean arterial pressure was monitored from a cannulated carotid artery, and heart rate was obtained from chest electrodes arranged for lead II. The jugular vein was cannulated for IV vehicle or drug administration in a volume of 1 ml/kg. Guinea pigs were sensitized with IP injections of ovalbumin 0.5 μg+Al(OH)$_3$ 1 mg (0.5 ml/animal) on days 1, and boosted with same dosage of ovalbumin and Al(OH)$_3$ vaccine on day 8; and the animals were ready to be challenged between days 19 and 23 to get a submaximal ovalbumin (50 μg/kg IV)-induced bronchoconstriction, reflected as an increase in tracheal pressure (cm $H_2O$). The animals were pretreated 5 minutes before test substance administration with IV indomethacin (10 mg/kg), mepyramine (2 mg/kg), and propranolol (0.1 mg/kg): a "cocktail" designed to inhibit the generation of cyclooxygenase products (thromboxanes, etc.) as well as antagonize histamine and β-adrenergic receptors. Test substances were administered PO (10 mg/kg) at 60 minutes before ovalbumin (50 μg/kg IV) challenge in 3 guinea pigs. Tracheal pressure, blood pressure and heart rate were measured immediately before and after ovalbumin challenge. A 50 percent or more (≧50%) inhibition of the induced bronchoconstriction relative to vehicle treated control animals was considered significant. The results are set forth in Tables 6-1 and 6-2, below.

TABLE 6-1

Pulmonary, Histamine $H_3$

| Compound | Route | Dose | N | Ind. | Inc. of TP (cm $H_2O$) X ± SEM | % INH. |
|---|---|---|---|---|---|---|
| Vehicle (Distilled Water) | PO | 5 ml/kg | 1 | 28.0 | | |
| | PO | 5 ml.kg | 2 | 20.0 | | |
| | PO | 5 ml/kg | 3 | 40.5 | 29.5 ± 6.0 | 0 |
| Peptide | PO | 10 mg/kg | 1 | 27.5 | | |
| | PO | 10 mg/kg | 2 | 35.5 | | |
| | PO | 10 mg/kg | 3 | 31.5 | 31.5 ± 2.3 | −6.8 |
| R-α-methylhistamine | IV | 30 mg/kg | 1 | 8.5 | | |
| | IV | 30 mg/kg | 2 | 25.0 | | |
| | IV | 30 mg/kg | 3 | 0.5 | 11.3 ± 7.2 | 61.6 |

A group of 3 guinea pigs were sensitized with IP injections of ovalbumin 0.5 μg + Al(OH)$_3$ 1 mg (0.5 ml/animal) on days 1 and day 8 and ready to be challenged between days 19 and 23. The animals were anesthetized with pentobarbital sodium and body temperature was maintained at 37° to 38° C. Test substances were administered PO (10 mg/kg) at 60 minutes before ovalbumin (50 μg/kg IV) challenge. Tracheal pressure, blood pressure and heart rate were measured immediately before and after ovalbumin challenge. A 50 percent or more (≧50%) inhibition of the induced bronchoconstriction relative to vehicle treated control animals was considered significant.

TABLE 6-2

Pulmonary, Histamine $H_3$

| Compound | Route | Dose | N | Pre-challenge | Post-challenge |
|---|---|---|---|---|---|
| Blood Pressure (mmHg) | | | | | |
| Vehicle (Saline) | PO | 5 ml/kg | 3 | 59.3 ± 4.1 | 44.0 ± 4.2 |
| Peptide | PO | 10 mg/kg | 3 | 60.7 ± 5.2 | 44.7 ± 0.7 |
| R-α-methylhistamine | IV | 30 mg/kg | 3 | 55.3 ± 1.3 | 34.0 ± 4.2 |
| Heart Rate (beats/min) | | | | | |
| Vehicle (Saline) | PO | 5 ml/kg | 3 | 228 ± 6.9 | 184 ± 10.6 |
| Peptide | PO | 10 mg/kg | 3 | 224 ± 4.0 | 188 ± 14.4 |
| R-α-methylhistamine | IV | 30 mg/kg | 3 | 232 ± 4.0 | 216 ± 0.0 |

A group of 3 guinea pigs were sensitized with IP injections of ovalbumin 0.5 μg + Al(OH)$_3$ 1 mg (0.5 ml/animal) on days 1 and day 8 and ready to be challenged between days 19 and 23. The animals were anesthetized with pentobarbital sodium and body temperature was maintained at 37° TO 38° C. Test substances were administered PO (10 mg/kg) at 60 minutes before ovalbumin (50 μg/kg IV challenge. Tracheal pressure, blood pressure and heart rate were measured immediately before and after ovalbumin challenge. A 50 percent or more (≧50%) inhibition of the induced bronchoconstriction relative to vehicle treated control animals was considered significant.
Total tested animals in this assay: 9 guinea pigs

EXAMPLE 9

In Vitro Screening of Peptide Activities

The peptide was further screened in vitro in a variety of enzyme and biochemical assays. Methods employed were adapted from the scientific literature to maximize reliability and reproducibility. The primary literature reference for each assay is listed in Table 11 opposite the results for each assay.

Unless otherwise indicated, the peptide was tested in duplicate at the concentrations indicated for each assay. Results presented in Table 10, "Results," are the average of duplicate determinations, unless otherwise noted.

Reference compounds were tested concurrently at 5 concentrations as an integral part of each assay to ensure the validity of the results obtained. Data inclusion criteria required that the $IC_{50}$ of the concurrently tested reference compound fall between ⅓ (0.33×) and 3 times (3×) the historical $IC_{50}$ of the reference compound (shown in Table 9, "Reference Compound Data").

Enzyme Assays

Enzyme assays were performed under conditions described in Table 8, "Experimental Conditions.". The commercial suppliers and catalog numbers of substrates employed in this study are given in Table 7, "Material Sources." The name, commercial source, and catalog numbers of concurrent reference compounds (controls) employed in this study are given in Table 9, "Reference Compound Data." The reaction catalyzed by each enzyme is listed in Table 8, "Experimental Conditions."

Radioligand Binding Assays

Radioligand binding assays were performed under conditions described in Table 8, "Experimental Conditions." Radioligands employed in this study are given in Table 8, and commercial sources and catalog numbers of the radioligands are provided in Table 7, "Material Sources." Unlabeled, blocking ligands employed this study are listed in Table 8, "Experimenal Conditions," along with the commercial sources and catalog number of the unlabeled ligand.

The concurrent reference compound (control) employed in each assay is listed in Table 9, "Reference Compound Data," along with the commercial supplier and catalog number of the compound. Sources of receptors or membrane preparations, whether from animal tissue or from recombinant expression, are provided in Table 7 as well. Where receptors have been obtained through recombinant expression techniques, the species from which the cDNA was obtained, and the type of expression system employed (mammalian, insect, bacterial) is also given Table 7.

Maximum total binding and nonspecific binding were determined each time each assay was run. Nonspecific binding was defined as the proportion of total binding not displaced by unlabeled ligand specific for the receptor. Specific binding was defined as the proportion of total binding that was displaced by unlabeled ligand. The unlabeled ligand and concentration employed are given Table 8, "Experimental Conditions."

Where presented, $IC_{50}$ values (defined as the concentration of test compound or competing ligand capable of displacing 50% of the specific binding of the radioligand) were determined by a non-linear, least squares regression analysis using GraphPad Prism Software (GraphPad, San Diego, Calif., USA). Where inhibition constants ($K_i$) are presented, the $K_i$ values were calculated using the equation of Cheng and Prusoff (Cheng, Y., Prusoff, W. H., Biochem. Pharmacol. 2:3099–3108, 1973) using the observed $IC_{50}$ of the tested compound, the concentration of radioligand employed in the assay, and the historical values for the $K_d$ of the ligand (obtained experimentally). Where presented, the Hill Coefficient ($n_H$), defining the scope of the competitive binding curve, was calculated using GraphPad Prism. Hill coefficients significantly different than 1.0, may suggest that the binding displacement does not follow the laws of mass action with a single binding site. Where $IC_{50}$, $K_i$, and/or Hill Slope data is presented without Standard Error of the Mean (SEM), data are insufficient to be quantitative, and the values presented ($K_i$, $IC_{50}$, nH) should be interpreted with caution.

Biochemical assay results are presented in Table 10, as the percent inhibition of specific binding or activity, and unless noted are the average of duplicate tubes tested at each concentration.

TABLE 7

MATERIAL SOURCES

| Target | Material Source | Rad.Ligand/ Substrate | Solvent |
|---|---|---|---|
| Collagenase IV | human U937 cells | NEN, Cat. #NET-660 | 0.4% DMSO |
| Cyclooxygenase-1 | ram seminal vesicle | Sigma, Cat #A-4425 | 1% DMSO |
| Cyclooxygenase-2 | sheep placenta | Sigma, Cat. #A-4425 | 1% DMSO |
| 5-Lipoxygenase | rat RBL-1 cells | Sigma, Cat. #A-9673 | 1% DMSO |
| $PLA_2$, Pancreatic | porcine pancreas | Amersham, Cat. #CFA-656 | 1% DMSO |
| Protease - Elastase | human neutrophils | Sigma, Cat. #M4765 | 1% DMSO |
| Ca++/Calmodulin Dep. PK II | rat brain | Panlabs, U.S. | 1% DMSO |
| Protein Kinase C, Non-Select. | rat brain | Sigma, Cat #H-5505 | 1% DMSO |
| Protein Kinase C - γ | rabbit brain (recombinant) | Sigma, Cat. #H-5505 | 1% DMSO |
| Ca++ Ch.-L, Benzothiazepine | rat cerebral cortex | NEN, Cat. #NET-847 | 0.4 DMSO |
| Ca++ Ch.-L, Dihydropyridine | rat cerebral cortex | NEN, Cat #NET-741 | 0.4% DMSO |
| Histamine $H_3$ | rat brain | NEN, Cat. #NET-1027 | 0.4% DMSO |
| Interleukin-1α | mouse Swiss/ 3T3 cells | Amersham, Cat. #IM-205 | 0.4% DMSO |
| Interleukin-6 | human U266 cells | NEN, Cat. #NEX-269 | 0.4% DMSO |
| Leukotriene $B_4$ | human U937 cells | Amersham, Cat. #TRK-692 | 0.4% DMSO |
| TNF-α | human U937 cells | NEN, Cat. #NEX-257 | 0.4% DMSO |

TABLE 8

EXPERIMENTAL CONDITIONS

| Cat. # | Assay Target | *Ligand/Substrate | 'Reaction or 'Nonspecific Ligand | Time/Temp |
|---|---|---|---|---|
| 11400 | Collagenase IV | [$^2$H]Denatured Collagen | [$^3$H]Collagen-[$^3$H]Peptides | 90 min. @ 37° C. |
| 11600 | Cyclooxygenase-1 | Arachidonic Acid | $AA-PGG_2-PGH_2-PGE_2$ | 20 min. @ 37° C. |
| 11800 | Cyclooxygenase-2 | Arachidonic Acid | $AA-PGG_2-PGH_2-PGE_2$ | 20 min. @ 37° C. |
| 13600 | 5-Lipoxygenase | Arachidonic Acid | AA-5-HPETE-5-HETE | 8 min. @ 25° C. |
| 16000 | $PLA_2$ Pancreatic | [$^{14}$c]3-phosphatidyl choline | Phosphatidylcholine-Palmitate | 5 min. @ 37° C. |
| 16600 | Protease - Elastase | MeOSuc-AAPV-pNa | Substrate-MeOSuc-AAPV + pNA | 10 min. @ 25° C. |

TABLE 8-continued

EXPERIMENTAL CONDITIONS

| Cat. # | Assay Target | *Ligand/Substrate | 'Reaction or ²Nonspecific Ligand | Time/Temp |
|---|---|---|---|---|
| 16800 | Ca++/Calmodulin Dep. PK II | BB40 | BB40 + [γ$^{32}$P]ATP-[$^{32}$P]BB40 + ADP | 5 min. @ 30° C. |
| 17800 | Protein Kinase C, Non-Select. | Histone H1 (HH1) | HH1 + [γ$^{32}$P]ATP-[$^{32}$ P]HH1 + ADP | 15 min. @ 25° C. |
| 18400 | Protein Kinase C - γ | Histone H1 (HH1) | HH1 + [γ$^{32}$P]ATP-[$^{32}$P]HH1 + ADP | 5 min. @ 30° C. |
| 21450 | Ca++ Ch.-L, Benzothiazepine | [$^3$H]Diltiazem | 10 μM Diltiazem; Kali-Chemie | 60 min. @ 37° C. |
| 21460 | Ca++Ch.-L, Dihydropyridine | [$^3$H]Nitrendipine | 1 μM Nifedipine; Sigma, Cat. #N-7634 | 90 min. @ 25° C. |
| 23980 | Histamine H. | [$^3$]NAMH | 1 μM NAMH; Sigma, Cat. #M-4910 | 30 min. @ 22° C. |
| 24350 | Interleukin-1α | [$^{25}$I]IL-1 alpha | 50 nM interleukin-1α; Pepro Tech EC, Cat. #200-01A | 120 min. @ 37° C. |
| 24410 | Interleukin-6 | [$^{125}$I]Interleukin-6 | 40 nM Interleukin-6; Pepro Tech EC, Cat. #200-06 | 16 hr. @ 4° C. |
| 25051 | Leukotriene B$_4$ | [$^{25}$H]LTB$_4$ | 2 μM Leukotriene B$_4$; Sigma, Cat. #L-0517 | 30 min. @ 25° C. |
| 28650 | THF-α | [125I]TNF-alpha | 50 nM TNF-α; R & D, Cat #210-TA | 3 hr. @ 4° C. |

*Radioligand or Enzyme Substrate,
¹Enzyme Assays Only,
²Unlabeled blocking ligand used for Radioligand Binding Assays Only,
§Criteria or brief description given for tissue, animal, and anti-infective assays

TABLE 9

REFERENCE COMPOUND DATA

| Cat. # | Target | $^1$K$_2$ | IB. | #Spec. | Ref. Cmpd. | Supplier | $^1$IC, | $^1$K$_1$ |
|---|---|---|---|---|---|---|---|---|
| 11400 | Collagenase IV | | | | HS—CH—R—CH(CH—CH(CH$_3$)$_2$—CO—Nal-Ala-NH | Peptides Int., Cat. #ISN-3835-PI | 31 nM | |
| 11600 | Cyclooxygenase-1 | | | | Indomethacin | Sigma, Cat. #I-7378 | 1.7 μM | |
| 11800 | Cyclooxygenase-2 | | | | Indomethacin | Sigma, Cat. #I7378 | 2.4 μM | |
| 13600 | 5-Lipoxygenase | | | | NDGA | Sigma, Cat #N-5023 | 0.26 μM | |
| 16000 | PLA$_2$ Pancreatic | | | | Quinacrine | Sigma, Cat. #Q3251 | 120 μM | |
| 16600 | Protease - Elastase | | | | N-Me—OSuc-AAPV | Sigma, Cat. #M-0398 | 180 nM | |
| 16800 | Ca++/Calmodulin Dep. PK II | | | | Trifluoperazine | Sigma. Cat. #T-8516 | 27 μM | |
| 17800 | Protein Kinase C, Non-Select | | | | H-7 | Sigma, Cat. #I-7016 | 35 μM | |
| 18400 | Protein Kinase C | | | | Staurosporine | Sigma, Cat. #S-4400 | 2.4 nM | |
| 21450 | Ca++Ch.-L, Benzothiazepine | 30 nM | 330 fmol/mg | 80% | Diltiazem | Kall-Cheml | 25 nM | 23 nM |
| 21460 | Ca++ Ch.-L, Dihydropyridine | 0.18 nM | 230 fmol/mg | 91% | Nifedipine | Sigma, Cat. #N-7634 | 2.7 nM | 1.7 nM |
| 23980 | Histamine H$_2$ | 0.35 nM | 13 fmol/mg | 85% | NAMH | Sigma, Cat. #M-4910 | 2.9 nM | 0.75 nM |

TABLE 9-continued

REFERENCE COMPOUND DATA

| Cat. # | Target | [1]$K_2$ | IB. | #Spec. | Ref. Cmpd. | Supplier | [1]IC | [1]$K_1$ |
|---|---|---|---|---|---|---|---|---|
| 24350 | Interleukin-1α | 0.18 nM | 4100 R/cell | 80% | IL-1 alpha | Pepro Tech EC, Cat. #200-01A | 31 pM | 23 pM |
| 24410 | Interleukin-6 | 0.06 nM | 670 R/cell | 80% | IL-6 | Pepro EC, Cat. #200-06 | 32 nMM | 1.4 nM |
| 25051 | Leukotriene B | 0.07 nM | 78 fmol/mg | 85% | LTB$_4$ | Sigma, Cat. #L-0517 | 0.2 nM | 0.05 nM |
| 28650 | TNF-α | 37 pM | 11 pmole/mg | 65% | TNF-alpha | R&D, Cat. #210-TA | 84 pM | 32 pM |

Historical values obtained are shown for each protocol,
[1]Historical $K_1$, $B_{max}$ and % Specific Binding are shown for radioligand binding assays and were experimentally determined by saturation analysis. Historical reference ligand $K_1$ values shown for binding assays only.

TABLE 10

RESULTS

| Target | [1]Spp. | Conc. | [1]% Inhibition | References |
|---|---|---|---|---|
| Collagenase IV | Hum | 100.0 μM | 2 | Morodomi, T., Ogata, Y., Sasaguri, Y., Morimatsu, M., Nagase, H. (1992) Purification and characterization of matrix metalloproteinase 9 from U937 moncytic leukaemia and HT 1080 fibrosarcoma cells. Biochem. J. Kato, Y., Ogawa, K., Yamamoto, S., Abe, S., Kishi, J., and Hayakawa, T. (1990) A novel TIMP-insensitive type IV collagen-degrading metalloproteinase from murine metastatic sarcoma. FEBS Lett. 268:39–42. Mallya, S.K., Mookhtiar, D.A., and Van Wart, H.E. (1986) Accurate, quantitative assays for the hydrolysis of soluble type I, II and III $^3$H-acetylated collagens by bacterial and tissue collagenases. Anal. Biochem. 158:334345, 1986. |
| Cyclo-oxygenase-1 | Ram | 300.0 μM | 2 | Boopathy, R. and Balasubramanian, A.S. (1988) Purification and characterization of sheep and platelet cyclooxygenase. Biochem. J 239:371–377. Evans, A.T., Formukong, E.A., and Evans, F.J. (1987) Action of cannabis constituents on enzymes of arachidonate metabolism: Anti-inflammatory potential. Biochem. Pharmacol. 36:2035–2037. |
| Cyclo-oxygenase-2 | Ov | 300.0 μM | 2 | O'Sullivan, M.G., Huggins, E.M. Jr., Meade, E.A., DeWitt, D.L., McCall, C.E. (1992) Lipopolysaccharide induces prostagladin H synthase-2 in alveolar macrophages. Biochem. Biophys. Res. Commun. 187:1123–1127. Evans, A.T. , Formukong, E.A., and Evans, F.J. (1987) Action of cannabis constituents on enzymes of arachidonate |

TABLE 10-continued

RESULTS

| Target | [1]Spp. | Conc. | [1]% Inhibition | References |
|---|---|---|---|---|
| | | | | metabolism: Anti-inflammatory potential. Biochem. Phamacol. 36:2035–2037. Boopathy, R. and Balasubramanian, A.S. (1988) Purification and characterization of sheep platelet cyclooxygenase. Biochem. J. 239:371–377. |
| 5-Lipoxygenase | Rat | 30.0 $\mu$M | 0 | Egan, R.W. and Gale, P.H. (1985) Inhibition of mammalian 5-lipoxygenase by aromatic disulfides. J. Biol. Chem. 260:11554–11559. Shimizu, T., Radmark, O., and Samuelsson, B. (1984) Enzyme with dual lipoxygenase activities catalyzes leukotriene $A_4$ synthetase from arachidonic acid. Proc. Natl. Acad. Sci. USA 81:689–693. |
| $PLA_2$, Pancreatic | Por | 300.0 $\mu$M | −11 | Katsumata, M., Gupta, C., Goldman, A.S. (1986) A rapid assay for activity of phospholipase $A_2$ using radioactive substrate. Anal. Biochem. 154:676–681. |
| Protease - Elastase | Hum | 30.0 $\mu$M | −11 | Baugh, R.J. and Travis, J. (1976) Human leukocyte granule elastase: rapid isolation and characterization. Biochemistry 14:836–841, 1976. |
| Ca++/Calmodulin Dep. PK II | Rat | 100.0 $\mu$M | 12 | Lai, Y., Nairn, A.C., Greengard, P. (1986) Autophosphorylation reversibly regulates the $Ca^{2+}$/calmodulin-dependence of $Ca^{2+}$/calmodulin dependent protein kinase II. Proc. Natl. Acad. Sci. USA 83:4253–4257. |
| Protein Kinase $C_1$ Non-Select. | Rat | 300.0 $\mu$M | −6 | Hannum, Y.A., Loomis, C.R., Bell, R.M. (1985) Activation of protein kinase C by Triton-X-100 mixed micelles containing diacylglycerol and phosphatidylserine. J. Biol. Chem. 260:10039–10043. Jeng, A.Y., Sharkey, N.A. and Blumberg, P.M. (1986) Purification of stable protein kinase C from mouse brain cytosol by specific ligand elution using fast protein liquid chromatography. Cancer res. 46:1966–1971. |
| Protein Kinase C - γ | Rab | 100.0 $\mu$M | −6 | Woddgett, J.R., and Hunter, T. (1987) Isolation and characterization of two distinct forms of protein kinase C.J. Biol. Chem. 262:4836–4843. |
| Ca++ Ch.-L, Benzothiazepine | Rat | 10.0 $\mu$M | 18 | Schoemaker, H. and Langer S.Z. (1985) [$^3$H]Diltiazem binding to calcium channel antagonist recognition sites in rat cerebral cortex. Eur. J. Pharmacol. 111:273–277. |
| Ca++ Ch.-L, Dihydro-pyridine | Rat | 10.0 $\mu$M | 2 | Gould R.J., Murphy, K.M.M., Snyder, S.H. (1982) [$^3$H]nitrendipine-labeled calcium channels discriminate inorganic calcium agonists and antagonists. Proc. Natl. Acad. Sci. USA 79:3656–3650. |

TABLE 10-continued

RESULTS

| Target | [1]Spp. | Conc. | [1]% Inhibition | References |
|---|---|---|---|---|
| | | | | Ehlert, F.J., Roeske, W.R., Itoga, E., and Yamamura, H.I. (1982) The binding of [$^3$H]nitrendipine to receptors for calcium channel antagonists in the heart, cerebral cortex and ileum of rats. Life Sci. 30:2191–2202. |
| Histamine $H_3$ | Rat | 10.0 μM | −13 | Korte, A., Myers, J., Shih, N.Y., Egan, R.W., Clark, M.A. (1990) Characterization and tissue distribution of $H_3$ histamine receptors in guinea pigs by N-alpha-methylhistamine. Biochem. Biophys. Res. Commun. 168:979–986. West Jr., R.E., Zweig, A., Shih, N.Y. Seigel, M.I., Egan, R.W., and Clark, M.A. (1990) Identification of two $H_3$-histamine receptor subtypes. Mol. Pharmacol. 38:610–613. |
| Interleukin-1α | Mus | 10.0 μM | 15 | Bird, T.A. and Saklatvaia J. (1986) Identification of a common class of high-affinity receptors for both types of porcine interleukin-1 on connective tissue cells. Nature 324:263–266. Chin, J., Cameron, P.M., Rupp, E., and Schmidt, J.A. (1987) Identification of a high affinity receptor for native interleukin-1 α and interleukin-1β on normal human lung fibroblasts. J. Exp. Med. 165:70–86. Killian, P.L. Kaffka, K.L. Stern, A.S., Woehle, D., Benjamin, W.R. Dechiara, T.M. Gubler, U., Farrar, J.J. Mizel, S.B., and Lomedico, P.T. (1986) Interleukin-1α and interleukin-1β bind to the same receptors on T cells. J. Immunol. 136:4509–4514. |
| Interleukin-6 | Hum | 10.0 μM | 13 | Taga, T., Hibi, M., Hirata, Y., Yamasaki, K., Yasukawa, K. Matsuda, T., Hirano, T., Kishimoto, T. (1989) Interleukin-6 triggers the association of its receptor with a possible signal transducer, gp 130. Cell 58:573–581. Cornfield, L.J., and Sills, M.A. (1991) High affinity interleukin-6 binding sites in bovine hypothalamus. Eur. J. Pharmacol. 202:113–115. |
| Leukotriene $B_4$ | Hum | 10.0 μM | 8 | Winkler, J.D., Sarau, H.M. Foley, J.J. Mong, S. Crooke, S.T. (1988) Leukotriene $B_4$-induced homologous desensitization of calcium mobilization and phosphoinositide metabolism in U-937 cells. J. Pharmacol. Exp. Ther. 246:204–210. |
| TNF-α | Hum | 10.0 μM | −11 | Yoshie, O., Tada, K., and Ishida, N. (1986) Binding and crosslinking of $^{125}$I labeled recombinant human tumor necrosis factor to cell surface receptors. J. Biochem. 100:531–541. |

TABLE 10-continued

RESULTS

| Target | [1]Spp. | Conc. | [1]% Inhibition | References |
|---|---|---|---|---|
| | | | | Maloff, B.L. and Delmendo, R.E. (1991) Development of a high-throughput binding assay for interleukin-1α(IL-1α) and tumor necrosis factor (TNF-α) in isolated membrane preparations. Agents and Actions 34:32–34. |

Negative values correspond to stimulation of binding or enzyme activity
[1]Bac = Bacteria; Bov = Bovine; Chi = Chicken; GP = Guinea Pig; Hum = Human; Mus = Mouse; Ov = Ovine; Por = Pig; Rab = Rabbit; SyH = Syrian Hamster; Yea-Yeast

EXAMPLE 10

In Vivo Anticancer Activity

The peptide was assayed in a mouse model of the tumor Sarcoma 180. This model has been used extensively as indicative of neovascularization in mammals inasmuch as the tumor so implanted is quickly vascularizing.

Experimental Design: All mice were weighed at test initiation and test termination. The animals were divided into three groups. The Sarcoma 180 tumor was made up from a passage mouse to furnish 2×1 viable cells per 0.1 mL inoculum. The cells were injected into the left leg hamstring muscle mass. The was delivered to the mice by I.P. injections, or gavage on days 1–5.

At the termination of the experiments, the mice were weighed and the left rear leg was amputated at the thigh. The skin was removed from the leg to expose the site at which the tumor was located. The net tumor weight was determined by subtracting the mean value obtained from 10 normal legs. The results are shown below in Table 11.

TABLE 11

Anti-Cancer Activity Against Mouse Tumor Sarcoma 180

| Test Material | No. of mice | Wt. gain, gm | Mean tumor wt. gain, gm | % tumor inhibition |
|---|---|---|---|---|
| Control, water | 10 | 6.2 | 2.3 | — |
| natural peptide @ 10 mg/kg | 6 | 5.8 | 0.03 | 99.0 |
| synthetic peptide (crude 60%) @ 10 mg/kg | 6 | 5.9 | 1.45 | 58.6 |

EXAMPLE 11

CAM Assay

The peptide was assayed in the CAM assay, so called, and inhibited proliferation of vacularization in that model by approximately 95%. Method: The method used was that described in D. Knighton, D. Ausprunk, D. Tapper, and J. Folkman, "Avascular and Vascular Phases of Tumour Growth in the Chick Embryo." *J. Cancer* 35:347–355 (1977) Procedure: The test compounds were suspended in sterile saline and then applied to methylcellulose discs, ¼ inch diameter with a micropipette and allowed to air dry at a concentration of 10 μg/disc.

The test was graded as follows:

| 0 | No change from control embryos |
|---|---|
| +1 | Slight inhibition of vasculature |
| +2 | Moderate inhibition of vasculature |
| +3 | Almost complete inhibition of vasculature |
| +4 | Complete inhibition of vasculature |

Results: The CAM assay antiangiogenesis scores are summarized in the table below. The following scores are based on the observation of at least 10 chick embryos. The results were as follows:

| Saline blank (neg. control) | 0.12 |
|---|---|
| Protamine/Hydrocortisone (positive control) | 2.7 |
| Peptide | 3.6 |

ADDITIONAL REFERENCES

1. Tatemoto, K., Rokaeus, A., Jornvall, H., McDonald, T. J., and Mutt, V. Galanin-A novel biologically active peptide from porcine intestine. FEBS Lett. 164: 124–128, 1983.
2. Hew, R. W. S., Hodgkinson, C. R., and Hill, S. J. Characterization of histamine $H_3$-receptor in guinea pig ileum with $H_3$-selective ligands. Br. J. Pharmacol. 101: 621–624, 1990.
3. Griswold, D. E., DiLorenzo, J. A. and Calabresi, P. Quantification and pharmacological dissection of oxazolone-induced contact sensitivity in the mouse. Cellular Immunology 11:198–204, 1974.
4. Hogaboam, C. M., Muller, M. J., Collins, S. M. and Hunt, R. H. An orally active non-selective endothelin receptor antagonist, bosentan, markedly reduces injury in a rat model of colitis. Eur. J. Pharmacol. 309: 261–269, 1996.
5. Chang, J., Blazek, Skowronek, M. Mariniari, L. and Carlson, R. P. The antiinflammatory action of guanabenz is mediated through 5-lipoxygenase and cyclooxygenase inhibition. Eur. J. Pharmacol. 142: 197–205, 1987.
6. Motaslm Billah, M., Chapman, R. W., Egan, R. W., Gilchrest, H., Piwinski, J. J., Sherwood, J., Siegel, M. I., West, Jr., R. E. and Kreutner, W. SCH 37370: a potent, orally active dual antagonist of platelet activating factor and histamine. J. Pharmacol. Exp. Ther. 252: 1090–1096, 1990.
7. Konzett, H. And Rossler, R. Versuensanordnung zu Untersuchungen an der Bronchialmuskulatur. Arch. Exp. Pathol. 195: 71–74, 1940.
8. Danko, G., Hey, J. A., Egan, R. W., Kretner, W. And Chapman, R. W. Histamine $H_3$ receptors inhibit sympathetic modulation of airway microvascular leakage in allergic guinea pigs. Eur. J. Pharmacol. 254: 283–286, 1994.

I claim:

1. A method for inhibiting an inflammatory response in a mammal in need thereof comprising administering to said mammal an effective amount of a peptide of the formula Leu-Pro-Pro-Ser-Arg (SEQ. ID 1).

2. The method of claim 1, wherein said mammal suffers from Inflammatory Bowel Disease.

3. The method of claim 2, wherein said mammal suffers from Crohn's disease.

4. The method of claim 1, wherein said peptide is administered by injection.

5. The method of claim 1, wherein said peptide is administered orally.

6. The method of claim 1, wherein said peptide is administered topically.

7. The method of claim 1, wherein said mammal is a human.

8. The method of claim 1, wherein said peptide is administered in a dose of about 2.5 mg/kg to about 500 mg/kg.

9. The method of claim 1, wherein said peptide is administered topically in a dose of 5 mg/kg to 100 mg/kg.

10. The method of claim 1, wherein said peptide is administered in a dose of 30 mg/kg.

* * * * *